US008551698B2

(12) United States Patent
Brown et al.

(10) Patent No.: US 8,551,698 B2
(45) Date of Patent: *Oct. 8, 2013

(54) METHOD OF LOADING SAMPLE INTO A MICROFLUIDIC DEVICE

(75) Inventors: James F. Brown, Clifton, VA (US); Jonathan E. Silver, Bethesda, MD (US)

(73) Assignees: Applied Biosystems, LLC, Carlsbad, CA (US); The United States Department of Health and Human Services, Washington, DC (US)

( * ) Notice: Subject to any disclaimer, the term of this patent is extended or adjusted under 35 U.S.C. 154(b) by 1101 days.

This patent is subject to a terminal disclaimer.

(21) Appl. No.: 11/837,608

(22) Filed: Aug. 13, 2007

(65) Prior Publication Data

US 2008/0138815 A1  Jun. 12, 2008

Related U.S. Application Data

(60) Continuation of application No. 10/798,857, filed on Mar. 11, 2004, which is a division of application No. 10/131,854, filed on Apr. 25, 2002, now Pat. No. 7,459,315, which is a division of application No. 09/563,714, filed on May 2, 2000, now Pat. No. 6,391,559, which is a division of application No. 08/838,262, filed on Apr. 17, 1997, now Pat. No. 6,143,496.

(51) Int. Cl.
*C12Q 1/68* (2006.01)

(52) U.S. Cl.
USPC .......................... 435/6.1; 435/91.1; 435/287.1

(58) Field of Classification Search
None
See application file for complete search history.

(56) References Cited

U.S. PATENT DOCUMENTS

| 2,561,339 | A | 7/1951 | Chediak |
| 3,389,966 | A | 6/1968 | Saravis |
| 3,390,962 | A | 7/1968 | Goldsmith |
| 3,691,017 | A | 9/1972 | Brown et al. |
| 3,865,548 | A | 2/1975 | Padawer |
| 4,065,263 | A | 12/1977 | Woodbridge, III |

(Continued)

FOREIGN PATENT DOCUMENTS

| DE | 3808942 A1 | 9/1989 |
| EP | 0229701 A2 | 7/1987 |

(Continued)

OTHER PUBLICATIONS

Simmonds et al., Human Immunodeficiency Virus-Infected Individuals Contain Provirus in Small Numbers of Peripheral Mononuclear Cells and at Low Copy Numbers, Journal of Virology, vol. 64, No. 2, Feb. 1990, pp. 864-872.

(Continued)

*Primary Examiner* — N. C. Yang
(74) *Attorney, Agent, or Firm* — O'Brien Jones PLLC

(57) ABSTRACT

A method comprising loading a sample into a microfluidic device which comprises plural sample chambers, subdividing the sample into a plurality of sample portions, such that respective sample portions are positioned in each of a plurality of the sample chambers, and subjecting the sample portions loaded into the respective sample chambers to at least a first amplification step. Each of the sample chambers has a respective volume such that if a sample portion positioned in the sample chamber comprises at least one molecule of a target nucleic acid, the target nucleic acid would attain a detectable concentration in the sample chamber after a single round of amplification.

41 Claims, 7 Drawing Sheets

(56) References Cited

U.S. PATENT DOCUMENTS

| | | | |
|---|---|---|---|
| 4,146,365 A | 3/1979 | Kay et al. | |
| 4,299,920 A | 11/1981 | Peters | |
| 4,468,371 A | 8/1984 | Chen et al. | |
| 4,483,925 A | 11/1984 | Noack | |
| 4,591,567 A | 5/1986 | Britten et al. | |
| 4,599,315 A | 7/1986 | Terasaki et al. | |
| 4,704,256 A | 11/1987 | Hood et al. | |
| 4,834,946 A | 5/1989 | Levin | |
| 4,868,130 A | 9/1989 | Hargreaves | |
| 4,911,782 A | 3/1990 | Brown | |
| 5,017,342 A | 5/1991 | Haberzettl et al. | |
| 5,041,266 A | 8/1991 | Fox | |
| 5,073,341 A | 12/1991 | Hargreaves | |
| 5,114,858 A | 5/1992 | Williams et al. | |
| 5,168,039 A | 12/1992 | Crawford et al. | |
| 5,169,766 A | 12/1992 | Schuster et al. | |
| 5,176,203 A | 1/1993 | Larzul | |
| 5,182,082 A | 1/1993 | Monthony et al. | |
| 5,184,020 A | 2/1993 | Hearst et al. | |
| 5,192,659 A | 3/1993 | Simons | |
| 5,194,370 A | 3/1993 | Berninger et al. | |
| 5,200,152 A | 4/1993 | Brown | |
| 5,225,332 A | 7/1993 | Weaver et al. | |
| 5,229,163 A | 7/1993 | Fox | |
| 5,229,297 A | 7/1993 | Schnipelsky et al. | |
| 5,276,125 A | 1/1994 | Pedain et al. | |
| 5,279,938 A | 1/1994 | Rosa | |
| 5,299,163 A | 3/1994 | Mortigami | |
| 5,304,487 A | 4/1994 | Wilding et al. | |
| 5,346,672 A | 9/1994 | Stapleton et al. | |
| 5,374,395 A | 12/1994 | Robinson et al. | |
| 5,376,252 A | 12/1994 | Ekstrom et al. | |
| 5,380,489 A | 1/1995 | Sutton et al. | |
| 5,415,839 A | 5/1995 | Zaun et al. | |
| 5,422,270 A | 6/1995 | Caspi | |
| 5,422,271 A | 6/1995 | Chen et al. | |
| 5,445,934 A | 8/1995 | Fodor et al. | |
| 5,447,679 A | 9/1995 | Eigen et al. | |
| 5,455,175 A | 10/1995 | Wittwer et al. | |
| 5,456,360 A | 10/1995 | Griffin | |
| 5,475,610 A | 12/1995 | Atwood et al. | |
| 5,494,795 A | 2/1996 | Guerry et al. | |
| 5,498,392 A * | 3/1996 | Wilding et al. | 422/68.1 |
| 5,503,803 A | 4/1996 | Brown | |
| 5,512,441 A | 4/1996 | Ronai | |
| 5,522,974 A | 6/1996 | Fishel et al. | |
| 5,525,464 A | 6/1996 | Drmanac et al. | |
| 5,526,705 A | 6/1996 | Skotnikov et al. | |
| 5,545,528 A | 8/1996 | Mitsuhashi et al. | |
| 5,571,410 A | 11/1996 | Swedberg et al. | |
| 5,576,176 A | 11/1996 | Adams et al. | |
| 5,580,722 A | 12/1996 | Foulkes et al. | |
| 5,580,730 A | 12/1996 | Okamoto | |
| 5,582,665 A | 12/1996 | Eigen et al. | |
| 5,585,069 A | 12/1996 | Zanzucchi et al. | |
| 5,587,128 A | 12/1996 | Wilding et al. | |
| 5,589,136 A | 12/1996 | Northrup et al. | |
| 5,601,982 A * | 2/1997 | Sargent et al. | 435/6 |
| 5,602,756 A | 2/1997 | Atwood et al. | |
| 5,610,016 A | 3/1997 | Sato et al. | |
| 5,614,396 A | 3/1997 | Bradley et al. | |
| 5,616,478 A | 4/1997 | Chetverin et al. | |
| 5,641,658 A | 6/1997 | Adams et al. | |
| 5,654,141 A | 8/1997 | Mariani et al. | |
| 5,674,742 A | 10/1997 | Northrup et al. | |
| 5,674,743 A | 10/1997 | Ulmer | |
| 5,716,825 A | 2/1998 | Hancock et al. | |
| 5,716,842 A | 2/1998 | Baier et al. | |
| 5,725,831 A | 3/1998 | Reichler et al. | |
| 5,766,851 A | 6/1998 | Shuldiner et al. | |
| 5,785,926 A | 7/1998 | Seubert et al. | |
| 5,795,748 A | 8/1998 | Cottingham | |
| 5,830,663 A | 11/1998 | Embleton et al. | |
| 5,846,727 A | 12/1998 | Soper et al. | |
| 5,856,100 A | 1/1999 | Hayashizaki | |
| 5,863,502 A * | 1/1999 | Southgate et al. | 422/58 |
| 5,871,908 A | 2/1999 | Henco et al. | |
| 5,876,930 A | 3/1999 | Livak et al. | |
| 5,939,312 A | 8/1999 | Baier et al. | |
| 5,948,673 A | 9/1999 | Cottingham | |
| 5,952,238 A | 9/1999 | Tsuji et al. | |
| 5,958,345 A | 9/1999 | Turner et al. | |
| 5,958,698 A | 9/1999 | Chetverin et al. | |
| 5,976,336 A | 11/1999 | Dubrow et al. | |
| 5,994,056 A | 11/1999 | Higuchi | |
| 6,001,568 A | 12/1999 | Chetverin et al. | |
| 6,027,873 A | 2/2000 | Schellenberger et al. | |
| 6,049,380 A | 4/2000 | Goodwin et al. | |
| 6,124,138 A | 9/2000 | Woudenberg et al. | |
| 6,126,899 A | 10/2000 | Woudenberg et al. | |
| 6,132,580 A | 10/2000 | Mathies et al. | |
| 6,143,496 A * | 11/2000 | Brown et al. | 435/6.11 |
| 6,171,785 B1 | 1/2001 | Higuchi | |
| 6,306,578 B1 | 10/2001 | Schellenberger et al. | |
| 6,379,929 B1 * | 4/2002 | Burns et al. | 435/91.2 |
| 6,387,331 B1 | 5/2002 | Hunter | |
| 6,391,559 B1 | 5/2002 | Brown et al. | |
| 6,436,632 B2 | 8/2002 | Schellenberger et al. | |
| 6,743,633 B1 | 6/2004 | Hunter | |
| 6,814,934 B1 | 11/2004 | Higuchi | |
| 6,825,047 B1 | 11/2004 | Woudenberg et al. | |
| 6,893,877 B2 | 5/2005 | Hunter et al. | |
| 7,081,226 B1 | 7/2006 | Wittwer et al. | |
| 7,211,443 B2 | 5/2007 | Woudenberg et al. | |
| 7,235,406 B1 | 6/2007 | Woudenberg et al. | |
| 7,244,622 B2 | 7/2007 | Woudenberg et al. | |
| 7,332,271 B2 | 2/2008 | O'Keefe et al. | |
| 7,381,569 B2 | 6/2008 | Woudenberg et al. | |
| 7,381,570 B2 | 6/2008 | Woudenberg et al. | |
| 7,381,571 B2 | 6/2008 | Woudenberg et al. | |
| 7,459,315 B2 | 12/2008 | Brown | |
| 7,547,556 B2 | 6/2009 | Hunter et al. | |
| 7,604,983 B2 | 10/2009 | O'Keefe et al. | |
| 7,666,360 B2 | 2/2010 | Schellenberger et al. | |
| 7,687,280 B2 | 3/2010 | Woudenberg et al. | |
| 7,833,711 B2 | 11/2010 | Woudenberg et al. | |
| 7,833,719 B2 | 11/2010 | O'Keefe et al. | |
| 7,888,108 B2 | 2/2011 | Woudenberg et al. | |
| 7,972,778 B2 * | 7/2011 | Brown et al. | 435/6.12 |
| 8,067,159 B2 * | 11/2011 | Brown et al. | 435/6.12 |
| 8,257,925 B2 * | 9/2012 | Brown et al. | 435/6.1 |
| 8,278,071 B2 * | 10/2012 | Brown et al. | 435/91.2 |
| 2001/0055765 A1 | 12/2001 | O'Keefe et al. | |
| 2001/0055812 A1 * | 12/2001 | Mian et al. | 436/45 |
| 2002/0119455 A1 | 8/2002 | Chan | |
| 2002/0151040 A1 | 10/2002 | O'Keefe et al. | |
| 2004/0171055 A1 | 9/2004 | Brown | |
| 2004/0171166 A1 | 9/2004 | Hunter | |
| 2004/0191924 A1 | 9/2004 | Hunter et al. | |
| 2005/0059074 A1 | 3/2005 | Schellenberger et al. | |
| 2005/0112634 A1 | 5/2005 | Woudenberg et al. | |
| 2005/0186684 A1 | 8/2005 | Woudenberg et al. | |
| 2006/0183151 A1 | 8/2006 | Woudenberg et al. | |
| 2006/0183171 A1 | 8/2006 | Schellenberger et al. | |
| 2006/0188917 A1 | 8/2006 | Woudenberg et al. | |
| 2006/0204401 A1 | 9/2006 | Woudenberg et al. | |
| 2006/0210439 A1 | 9/2006 | Woudenberg et al. | |
| 2007/0042419 A1 | 2/2007 | Barany et al. | |
| 2007/0111299 A1 | 5/2007 | Woudenberg et al. | |
| 2007/0111300 A1 | 5/2007 | Woudenberg et al. | |
| 2007/0134710 A1 | 6/2007 | Woudenberg et al. | |
| 2008/0102461 A1 | 5/2008 | Woudenberg et al. | |
| 2008/0102462 A1 | 5/2008 | Woudenberg et al. | |
| 2008/0108068 A1 | 5/2008 | Woudenberg et al. | |
| 2008/0108112 A1 | 5/2008 | O'Keefe et al. | |
| 2008/0153091 A1 | 6/2008 | Brown et al. | |
| 2008/0160525 A1 | 7/2008 | Brown et al. | |
| 2008/0169184 A1 | 7/2008 | Brown et al. | |
| 2008/0171324 A1 | 7/2008 | Brown et al. | |
| 2008/0171325 A1 * | 7/2008 | Brown et al. | 435/6 |
| 2008/0171326 A1 | 7/2008 | Brown et al. | |
| 2008/0171327 A1 | 7/2008 | Brown et al. | |
| 2008/0171380 A1 | 7/2008 | Brown et al. | |
| 2008/0171382 A1 | 7/2008 | Brown et al. | |

(56) References Cited

U.S. PATENT DOCUMENTS

| | | | |
|---|---|---|---|
| 2008/0213766 A1* | 9/2008 | Brown et al. ............... 435/6 |
| 2009/0035759 A1 | 2/2009 | Brown et al. |
| 2009/0258797 A1 | 10/2009 | Hunter et al. |
| 2010/0075330 A1 | 3/2010 | O'Keefe et al. |
| 2010/0173394 A1 | 7/2010 | Colston, Jr. et al. |
| 2011/0003281 A1 | 1/2011 | Woudenberg et al. |
| 2011/0065590 A1 | 3/2011 | Hunter |
| 2011/0311978 A1 | 12/2011 | Makarewicz, Jr. et al. |
| 2011/0311979 A1 | 12/2011 | Brown |
| 2012/0063972 A1 | 3/2012 | Brown et al. |
| 2012/0301884 A1 | 11/2012 | Brown et al. |

FOREIGN PATENT DOCUMENTS

| | | |
|---|---|---|
| EP | 0320240 A1 | 6/1989 |
| EP | 0164054 B1 | 8/1989 |
| EP | 0346594 A1 | 12/1989 |
| EP | 0366448 A2 | 5/1990 |
| EP | 0370719 A2 | 5/1990 |
| EP | 0392546 A2 | 10/1990 |
| EP | 0420260 A2 | 4/1991 |
| EP | 0435150 A2 | 7/1991 |
| EP | 0487218 A1 | 5/1992 |
| EP | 0502011 A1 | 9/1992 |
| EP | 0512334 A2 | 11/1992 |
| EP | 0549107 A1 | 6/1993 |
| EP | 0502011 B1 | 6/1994 |
| EP | 0632128 A1 | 1/1995 |
| EP | 0643140 A1 | 3/1995 |
| EP | 0676643 A2 | 10/1995 |
| EP | 0716150 A1 | 6/1996 |
| EP | 0747488 A1 | 12/1996 |
| EP | 0751394 A1 | 1/1997 |
| EP | 0761822 A2 | 3/1997 |
| EP | 0774516 A2 | 5/1997 |
| EP | 0872562 A1 | 10/1998 |
| EP | 0512334 B1 | 9/1999 |
| EP | 0872562 B1 | 9/2002 |
| EP | 1256631 A1 | 11/2002 |
| EP | 0872562 B2 | 12/2009 |
| WO | WO 89/08717 A1 | 9/1989 |
| WO | WO 89/09282 A1 | 10/1989 |
| WO | WO 89/09437 A1 | 10/1989 |
| WO | WO 89/10413 A1 | 11/1989 |
| WO | WO 89/10977 A1 | 11/1989 |
| WO | WO 89/10979 A1 | 11/1989 |
| WO | WO 89/11546 A1 | 11/1989 |
| WO | WO 90/06374 A1 | 6/1990 |
| WO | WO 90/10718 A1 | 9/1990 |
| WO | WO 90/11369 A1 | 10/1990 |
| WO | WO 90/15881 A1 | 12/1990 |
| WO | WO 91/06571 A1 | 5/1991 |
| WO | WO 91/07505 A1 | 5/1991 |
| WO | WO 91/09973 A2 | 7/1991 |
| WO | WO 91/15516 A2 | 10/1991 |
| WO | WO 91/16966 A1 | 11/1991 |
| WO | WO 91/18114 A1 | 11/1991 |
| WO | WO 91/19813 A1 | 12/1991 |
| WO | WO 92/01812 A1 | 2/1992 |
| WO | WO 92/05443 A1 | 4/1992 |
| WO | WO 92/13092 A1 | 8/1992 |
| WO | WO 92/18608 A1 | 10/1992 |
| WO | WO 93/10150 A1 | 5/1993 |
| WO | WO 93/16194 A1 | 8/1993 |
| WO | WO 93/22058 A1 | 11/1993 |
| WO | WO 93/25706 A1 | 12/1993 |
| WO | WO 94/04918 A1 | 3/1994 |
| WO | WO 95/02067 A1 | 1/1995 |
| WO | WO 95/11454 A1 | 4/1995 |
| WO | WO 95/14109 A1 | 5/1995 |
| WO | WO 95/21269 A1 | 8/1995 |
| WO | WO 95/21382 A2 | 8/1995 |
| WO | WO 95/30774 A1 | 11/1995 |
| WO | WO 96/05861 A1 | 2/1996 |
| WO | WO 96/14430 A1 | 5/1996 |
| WO | WO 96/15450 A1 | 5/1996 |
| WO | WO 96/18731 A2 | 6/1996 |
| WO | WO 96/24677 A1 | 8/1996 |
| WO | WO 96/26291 A1 | 8/1996 |
| WO | WO 96/36736 A2 | 11/1996 |
| WO | WO 96/39176 A1 | 12/1996 |
| WO | WO 96/39536 A1 | 12/1996 |
| WO | WO 96/41012 A1 | 12/1996 |
| WO | WO 97/03207 A1 | 1/1997 |
| WO | WO 97/06890 A1 | 2/1997 |
| WO | WO 97/10056 A2 | 3/1997 |
| WO | WO 97/20951 A1 | 6/1997 |
| WO | WO 97/22825 A1 | 6/1997 |
| WO | WO 97/32040 A2 | 9/1997 |
| WO | WO 97/48818 A1 | 12/1997 |
| WO | WO 98/22625 A1 | 5/1998 |
| WO | WO 98/26098 A1 | 6/1998 |
| WO | WO 98/38487 A2 | 9/1998 |
| WO | WO 98/45481 A1 | 10/1998 |
| WO | WO 98/46438 A1 | 10/1998 |
| WO | WO 98/46797 A1 | 10/1998 |
| WO | WO 98/47003 A1 | 10/1998 |

OTHER PUBLICATIONS

Simmonds et al., Analysis of Sequence Diversity in Hypervariable Regions of the External Glycoprotein of Human Immunodeficiency Virus Type 1, Journal of Virology, vol. 64, No. 12, Dec. 1990, pp. 5840-5850.

Wittwer et al., "The LIGHTCYCLER™: A Microvolume Multisample Flourimeter With Rapid Temperature Control"; *BioTechniques*, vol. 22, No. 1; pp. 176-181 (Jan. 1997).

Woolley et al; "Ultra-High-Speed DNA Fragment Separations Using Microfabricated Capillary Array Electrophoresis Chips"; *Proc. Natl. Acad. Sci. USA*, vol. 91, pp. 11348-11352, *Biophysics*, (1994).

Wilding et al., PCR in a Silicone Mircrostructure, *Clinical Chemistry*, vol. 40, No. 9, pp. 1815-1818 (1994).

Good et al.; Generalization of Theory for Estimation of Interfacial Energies; *Chemistry and Physics of Interfaces*, ACS, pp. 91-96 (1971).

Burns et al.; Microfabricated Structures for Integrated DNA Analysis; *Proc. Natl Acad. Sci. USA*, vol. 93, pp. 5556-5561, Genetics (1996).

Rigler, "Fluorescence Correlations, Single Molecule Detection and Large Number Screening Applications in Biotechnology"; *Journal of Biotechnology*, vol. 41, pp. 177-186 (1995).

Cheng et al.; "Analysis of Ligase Chain Reaction Products Amplified in a Silicon-Glass Chip Using Capillary Electrophoresis", *Journal of Chromatography*, vol. 732, pp. 151-158 (1996).

Krioka et al.; "Imaging of Chemiluminescent Reactions in Mesocale Silicon-Glass Microstructures"; *J. Biolumin Chemilumin*, vol. 9; pp. 135-138 (1994).

Woolley et al., "Ultra-High-Speed DNA Sequencing Using Capillary Electrophoresis Chips"; *Anal-Chem*, vol. 67, No. 20, pp. 3676-3680 (1995).

Hawkins et al.; "Incorporation of a Fluorescent Guanosine Analog Into Oligonucleotides and Its Application to a Real Time Assay for the HIV-1 INTEGRASE 3'-Processing Reaction"; *Nucleic Acids Research*, vol. 23, No. 15, pp. 2872-2880 (1995).

Tyagi et al.; "Molecular Beacons: Probes That Fluoresce Upon Hybridization" *Nature Biotechnology*, vol. 14, pp. 303-308 (1996).

Holland et al,; Detection of Specific Polymerase Chain Reaction Product by Utilizing the 5'→ 3' Exonuclease Activity of *Thermus aquaticus* DNA Polymerase; *Proc. Natl. Acad. Sci.*, vol. 88, *Biochemistry*, pp. 7276-7280 (1991).

Livak et al.; "Oligonucleotides With Fluorescent Dyes at Opposite Ends Provide a Quenched Probe System Useful for Detecting PCR Product and Nucleic Acid Hybridization"; *PCR Method and Applications*, pp. 357-362 (1995).

Sninsky et al.; "The Application of Quantitative Polymerase Chain Reaction to Therapeutic Monitoring"; AIDS, vol. 7 (Supp 2), pp. S29-S34 (1993).

(56) References Cited

OTHER PUBLICATIONS

Becker-André et al., Absolute mRNA Quantification Using the Polymerase Chain Reaction (PCR); *Nucleic Acids Research*, vol. 17, No. 22, pp. 9437-9446 (1989).

Gilliland et al.; "Analysis of Cytokine mRNA and DNA: Detection and Quantitation by Competitive Polymerase Chain Reaction", *Proc. Natl. Acad. Sci. USA*, vol. 87, Genetics, pp. 2725-2729 (1990).

Higuchi et al.; "Simultaneous Amplification and Detection of Specific DNA Sequences"; *Biotechnology*; vol. 10, pp. 413-417 (1992).

Held et al.; "Real Time Quantitative PCR", *Genome Research*, No. 6, pp. 986-994 (1996).

Gibson et al.; "A Novel Method for Real Time Quantitative RT-PCR"; *Genome Research*, No. 6, pp. 995-1001 (1996).

Gerard et al.; "A Rapid and Quantitative Assay to Estimate Gene Transfer Into Retrovirally Transduced Hematopoietic Stem/Progenitor Cells Using a 96-Well Format PCR and Fluorescent Detection System Universal for MMLV-Based Proviruses"; *Human Gene Therapy*, No. 7, pp. 343-354 (1996).

Wittwer et al., "Rapid Cycle DNA Amplification", *Biotechniques*, vol. 10, No. 1, pp. 76-83 (1991).

Chang, *Physical Chemistry With Applications to Biological Systems*, $2^{nd}$ Edition, Sec. 5.4, p. 87, 1977.

Berg, *Random Walks in Biology*, "Diffusion: Microscopic Theory", pp. 10, 49 (1983).

Burns et al.; Microfabricated Structures for Integrated DNA Analysis, *Proc. Natl. Acad. Sci.*, vol. 93, Genetics, pp. 5556-5561 (1996).

Cheng et al.; Chip PCR. II. Investigation of Different PCR Amplification Systems in Microfabricated Silicon-Glass Chips; *Nucleic Acids Research*, vol. 24, No. 2, pp. 380-385 (1996).

Woolley et al.; "Functional Integration of PCR Amplification and Capillary Electrophoresis in a Microfabricated DNA Analysis Device"; *Anal Chem.* No. 68, pp. 4081-4086 (1996).

Wittwer et al; Continuous Fluorescence Monitoring of Rapid Cycle DNA Amplification; *Biotechniques*, 22, pp. 130-138 (Jan. 1997).

Hawkins et al.; Fluorescence Properties of Pteridine Nucleoside Analogs As Monomers and Incorporated Into Oligonucleotides, *Analytical Biochemistry*, 244, pp. 86-95 (1997).

Xu et al., "Direct Measurement of Single-Molecule Diffusion and Photodecomposition in Free Solution", *Science*, vol. 275, pp. 1106-1109 (Feb. 1997).

*CRC Handbook of Chemistry and Physics*, $74^{th}$ Edition, Lide (Editor-In-Chief), p. 6-10 (1993-1994).

Abstract of Li et al., Direct Electrophoretic Detection of the Allelic State of Single DNA Molecules in Human Sperm by Using the Polymerase Chain Reaction, *Proc. Nat'l Acad. Sci. USA*, 87 (12), pp. 4580-4584 (Jun. 1990).

Abstract of Nakamura et al., Amplification and Detection of a Single Molecule of Human Immunodeficiency virus RNA, *Virus Genes*, 7(4), pp. 325-338 (Dec. 1993).

Abstract of Stephens et al., Theoretical Underpinning of the Single-Molecule-Dilution (SMD) Method of Direct Haplotype Resolution, *Am. J. Hum. Genet.*, 46(6), pp. 1149-1155, Department of Human Genetics, Yale University School of Medicine, New Haven, CT 06511 (Jun. 1990).

Abstract of Jena et al., Amplification of Genes, Single Transcripts and cDNA Libraries From One Cell and Direct Sequence Analysis of Amplified Products Derived From One Molecule, *J. Immun. Mthds*, 190(2), pp. 199-213 (Apr. 19, 1996).

Jena et al., *Amplification of genes, single transcripts and cDNA libraries from one cell and direct sequence analysis of amplified products derived from one molecule*, Journal of Immunological Methods 190 (1996) pp. 199-213.

Ruano et al., *Haplotype of Multiple Polymorphisms Resolved by Enzymatic Amplification of Single DNA Molecules*, Proceedings of the National Academy of Sciences of the United States of America, vol. 87, Issue 16, Aug. 1990, pp. 6296-6300.

Applied Biosystems, SOLiD™ System, Sequencing by Oligonucleotide Ligation and Detection, pp. 1-37, 2006.

Sykes et al., *Quantitation of Targets for PCR by Use of Limiting Dilution*, Research Report, BioTechniques, vol. 13, No. 3 (1992), pp. 444-449.

Chetverina et al., *Cloning of RNA molecules in vitro*, Nucleic Acids Research, 1993, vol. 21, No. 10, pp. 2349-2353.

Newton et al., *Analysis of any point mutation in DNA. The amplification refractory mutation system (ARMS)*, Nucleic Acids Research, vol. 17, No. 7, 1989, pp. 2503-2516.

Voss et al., *Direct genomic fluorescent on-line sequencing and analysis using in vitro amplification of DNA*, Nucleic Acids Research, vol. 17, No. 7, 1989, pp. 2517-2526.

Lamture et al., *Direct detection of nucleic acid hybridization on the surface of a charge coupled device*, Nucleic Acids Research, vol. 22, No. 11, 1994, pp. 2121-2125.

Ed M. Southern, *DNA chips: analysing sequence by hybridization to oligonucleotides on a large scale*, TIG, vol. 12, No. 3, Mar. 1996, pp. 110-115.

Edwin M. Southern, *High-density gridding: techniques and applications*, Analytical biotechnology, Biotechnology 1996, vol. 7, pp. 85-88.

Van Ness et al., *A versatile solid support system for oligodeoxynucleotide probe-based hybridization assays*, Nucleic Acids Research, vol. 19, No. 12, 1991, pp. 3345-3350.

Käller et al., *Arrayed identification of DNA signatures*, Review, Future Drugs Ltd., 2007, pp. 65-76.

Mardis, Elaine R., *The impact of next-generation sequencing technology on genetics*, Review, Cell Press, Available online Feb. 11, 2008, pp. 133-141.

Shendure et al., *Overview of DNA Sequencing Strategies*, DNA Sequencing, Supplement 81, Current Protocols in Molecular Biology 7.1.1-7.1.11, Jan. 2008, pp. 1-11.

DNA Sequencing, Illumina Sequencing Kits, Single-Read Sequencing, Paired-End Sequencing, Chromatin Immunoprecipitation Sequencing (CHIP-SEQ), www.illumina.com, pp. 58-79, 2007.

Lukyanov et al., *Molecule by molecule PCR amplification of complex DNA mixtures for direct sequencing: an approach to vitro cloning*, Nucleic Acids Research, vol. 24, No. 11, 1996, pp. 2194-2195.

*Digital (or Clonal) PCR is an Essential Part of processes for Second Generation Sequencing*, www.genomicnanosytems.com/naturemethodsjan2008.html, Jan. 2008, pp. 1-4.

Illumina® Systems & Software, *DNA Sequencing with Solexa® Technology*, Technology Spotlight, Pub. No. 770-2007-002, May 1, 2007, pp. 1-4.

Cavalieri, Liebe F., et al., "A DNA-Acrylamide Gel Column For Analyzing Proteins That Bind to DNA, I. DNA Polymerase," Proceedings of the National Academy of Sciences, Oct. 1970, vol. 67, No. 2, pp. 807-812.

Klibanov, Alexander M., "Immobilized Enzymes and Cells as Practical Catalysts," *Science*, Feb. 1983, vol. 219, pp. 722-727.

Wong, Corinne et al., "Characterization of β-thalassaemia mutations using direct genomic sequencing of amplified single copy DNA," *Nature*, Nov. 26, 1987, vol. 330, pp. 384-386.

Chibata, Ichiro et al., "Immobilization of Cells in Carrageenan," *Methods in Enzymology*, 1987, vol. 135, pp. 189-198.

Primrose, S. B., *Modern Biotechnology*, Oxford, Blackwell Scientific Publications, 1987, pp. 85-93.

Mullis, Kary B., et al, "Specific Synthesis of DNA in Vitro via a Polymerase-Catalyzed Chain Reaction," *Methods in Enzymology*, 1987, vol. 155, pp. 335-350.

Higuchi, Russell et al., "DNA typing from single hairs," *Nature*, Apr. 7, 1988, vol. 332, pp. 543-546.

Church, GM et al., "Multiplex DNA Sequencing," *Science*, Apr. 8, 1988, vol. 240, No. 4849, pp. 185-188.

Saiki, Randall K., et al., "Primer-Directed Enzymatic Amplification of DNA with a Thermostable DNA Polymerase," *Science*, Jan. 29, 1988, vol. 239, No. 4839, pp. 487-491.

Rensberger, Boyce, "Magazine Award: Molecule of the Year," *The Washington Post*, Dec. 25, 1989, A Section, A2.

Chehab, Farid F., et al., "Detection of specific DNA sequences by fluorescence amplification: A color complementation assay," Proc. Nati. Acad. Sci. USA, Dec. 1989, vol. 86, pp. 9178-9182.

(56) References Cited

OTHER PUBLICATIONS

Larzul, Daniel et al., "A non-radioactive diagnostic test for the detection of HBV DNA sequences in serum at the single molecule level," *Molecular and Cellular Probes*, Mar. 1989, vol. 3, No. 1, pp. 45-57.
White, Thomas J., et al., "The polymerase chain reaction," *Trends in Genetics*, Jun. 1989, vol. 5, No. 6, pp. 185-189.
Green, Eric D., et al., "Systematic screening of yeast artificial-chromosome libraries by use of the polymerase chain reaction," Proc. Natl. Acad. Sci. USA, Feb. 1990, vol. 87, pp. 1213-1217.
Chetverin, Alexander B., et al., "On the Nature of Spontaneous RNA Synthesis by Qβ Replicase," *Journal of Molecular Biology*, 1991, vol. 222, pp. 3-9.
Kuzmin et al., *Mol Gen Mikrobiol Virusol*, 1991, vol. 8, pp. 6-8.
Monckton, Darren G., et al., "Minisatellite "isoallele" discrimination in pseudohomozygotes by single molecule PCR and variant repeat mapping," *Genomics*, Oct. 1991, vol. 11, No. 2, pp. 465-467.
Parimoo, Satish et al., "cDNA selection: Efficient PCR approach for the selection of cDNAs encoded in large chromosomal DNA fragments," Proc. Natl. Acad. Sci. USA, Nov. 1991, vol. 88, pp. 9623-9627.
Yolken, Robert H., et al., "Solid phase capture method for the specific amplification of microbial nucleic acids—avoidance of false-positive and false-negative reactions," *Molecular and Cellular Probes*, 1991, vol. 5, pp. 151-156.
Chiu, Kuo-Ping et al., "Intracellular Amplification of Proviral DNA in Tissue Sections Using the Polymerase Chain Reaction," *Analytical Biochemistry*, 1992, vol. 40, No. 3, pp. 333-341.
Levesque, Georges et al., "Biochemical Manipulations of Minute Quantities of mRNAs and cDNAs Immobilized on Cellulose Paper Discs," *Methods in Enzymology*, vol. 216, pp. 179-186.
Yourno, Joseph, "A Method for Nested PCR with Single Closed Reaction Tubes," *PCR Methods and Applications*, pp. 60-65.
Toranzos, Gary A., et al., "Solid-phase polymerase chain reaction: applications for direct detection of enteric pathogens in waters," *Canadian Journal of Microbiology*, 1992, vol. 38, pp. 365-369.
Galindo, Ivan et al., "A combined polymerase chain reaction-colour development hybridization assay in a microtitre format for the detection of *Clostridium* spp.," *Applied Microbiology and Biotechnology*, Jul. 1993, vol. 39, No. 4-5, pp. 553-557.
Mizukoshi, Noriko et al., "Detection of African Horsesickness Virus by Reverse Transcriptase Polymerase Chain Reaction (RT-PCR) using Primers for Segment 5 (NS1 Gene)," *The Journal of Veterinary Medical Science*, Apr. 1994, vol. 56, No. 2, pp. 347-352.
Rasmussen, Soren R. et al., "Combined Polymerase Chain Reaction-Hybridization Microplate Assay Used to Detect Bovine Leukemia Virus and *Salmonella*," *Clinical Chemistry*, 1994, vol. 40, No. 2, pp. 200-205.
Komminoth, P., et al., "In situ Polymerase Chain Reaction: General Methodology and Recent Advances," *Verh. Dtsch. Ges. Path.*, 1994, vol. 78, pp. 146-152.
Burg, Lawrence J., et al., "Single molecule detection of RNA reporter probes by amplification with Qβ replicase," *Molecular and Cellular Probes*, Aug. 1996, vol. 10, No. 4, pp. 257-271.
Shoffner, Mann A., et al., "Chip PCR. I. Surface passivation of microfabricated silicon-glass chips for PCR," *Nucleic Acids Research*, 1996, vol. 24, No. 2, pp. 375-379.
Chang, Tsung C., et al., "A modified immuno-polymerase chain reaction for the detection of β-glucuronidase from *Escherichia coli*," *Journal of Immunological Methods*, Oct. 1997, vol. 208, No. 1, pp. 35-42.
Chen, Zhong-Ping et al., "Quantitation of ERCC-2 Gene Expression in Human Tumor Cell Lines by Reverse Transcription-Polymerase Chain Reaction in Comparison to Northern Blot Analysis," *Analytical Biochemistry*, Jan. 1997, vol. 244, No. 1, pp. 50-54.
Kalinina, Olga et al., "Nanoliter scale PCR with TaqMan detection," *Nucleic Acids Research*, 1997, vol. 25, No. 10, pp. 1999-2004.
Monckton, Darren G., et al., "Somatic mosaicism, germline expansions, germline reversions and intergenerational reductions in myotonic dystrophy males: small pool PCR analyses," *Human Molecular Genetics*, 1995, vol. 4, No. 1, pp. 1-8.

Office Action dated Mar. 3, 1999 from U.S. Appl. No. 08/838,262.
Office Action dated Aug. 31, 1999 from U.S. Appl. No. 08/838,262.
Office Action dated Dec. 15, 2004 from U.S. Appl. No. 10/131,854.
Office Action dated Aug. 22, 2005 from U.S. Appl. No. 10/131,854.
Office Action dated Sep. 22, 2006 from U.S. Appl. No. 10/131,854.
Office Action dated Jan. 9, 2007 from co-pending U.S. Appl. No. 10/798,857.
Office Action dated Oct. 5, 2007 from co-pending U.S. Appl. No. 10/798,857.
Office Action dated Mar. 19, 2009 from co-pending U.S. Appl. No. 10/798,857.
Office Action dated May 14, 2009 from co-pending U.S. Appl. No. 11/837,559.
Office Action dated Apr. 14, 2010 from co-pending U.S. Appl. No. 11/837,559.
Office Action dated May 28, 2009 from abandoned U.S. Appl. No. 11/837,561.
Office Action dated Feb. 17, 2010 from abandoned U.S. Appl. No. 11/837,561.
Office Action dated Apr. 16, 2010 from co-pending U.S. Appl. No. 11/837,564.
Office Action dated Nov. 24, 2010 from co-pending U.S. Appl. No. 11/837,564.
Office Action dated Apr. 1, 2010 from co-pending U.S. Appl. No. 11/837,565.
Office Action dated Nov. 23, 2009 from abandoned U.S. Appl. No. 11/837,569.
Office Action dated Mar. 18, 2010 from co-pending U.S. Appl. No. 11/837,581.
Office Action dated Jul. 22, 2010 from co-pending U.S. Appl. No. 11/837,600.
Office Action dated Mar. 4, 2010 from co-pending U.S. Appl. No. 11/837,613.
Office Action dated Nov. 24, 2010 from co-pending U.S. Appl. No. 11/837,613.
Office Action dated Mar. 3, 2010 from co-pending U.S. Appl. No. 11/837,620.
Office Action dated Nov. 24, 2010 from co-pending U.S. Appl. No. 11/837,620.
Office Action dated Mar. 5, 2010 from co-pending U.S. Appl. No. 11/837,651.
Office Action dated May 14, 2010 from co-pending U.S. Appl. No. 11/837,656.
Office Action dated Feb. 29, 2012 from co-pending U.S. Appl. No. 11/837,581.
Office Action dated Sep. 22, 2011 from co-pending U.S. Appl. No. 11/837,656.
Office Action dated Dec. 15, 2011 from co-pending U.S. Appl. No. 13/108,959.
Response dated Jan. 20, 2012 from co-pending U.S. Appl. No. 11/837,564.
Response dated Nov. 30, 2011 from co-pending U.S. Appl. No. 11/837,581.
Response dated Jan. 23, 2012 from co-pending U.S. Appl. No. 11/837,656.
Haff, L., et al., "A High-Performance System for Automation of the Polymerase Chain Reaction," *BioTechniques*, Jan. 1991, vol. 10, No. 1, pp. 102-103, 106-112.
Garner, Harold R., et al., "High-Throughput PCR," *Biotechniques*, 1993, vol. 14, No. 1, pp. 112-115.
Noguchi, Shinzaburo et al., "The Detection of Breast Carcinoma Micrometastases in Axillary Lymph Nodes by Means of Reverse Transcriptase-Polymerase Chain Reaction," *Cancer*, Sep. 1, 1994, vol. 74, No. 5, pp. 1595-1600.
Sasaki, Nobuya, "Development of High-throughput Polymerase Chain Reaction System and Its Performance," *Hokkaido J. Med. Sci.*, May 1997, vol. 72, No. 3, pp. 249-259.
Office Action dated Jun. 11, 2008 from co-pending U.S. Appl. No. 10/798,857.
Office Action dated Mar. 10, 2011 from co-pending U.S. Appl. No. 11/837,564.
Office Action dated Dec. 21, 2010 from co-pending U.S. Appl. No. 11/837,565.

(56) References Cited

OTHER PUBLICATIONS

Office Action dated Mar. 11, 2011 from co-pending U.S. Appl. No. 11/837,581.
Office Action dated Nov. 26, 2010 from co-pending U.S. Appl. No. 11/837,651.
Office Action dated Dec. 16, 2010 from co-pending U.S. Appl. No. 11/837,656.
Office Action dated Mar. 31, 2011 from co-pending U.S. Appl. No. 11/837,656.
Response to Office Action dated Jun. 3, 1999 from U.S. Appl. No. 08/838,262.
Response to Office Action dated Nov. 12, 1999 from U.S. Appl. No. 08/838,262.
Response to Office Action dated Jun. 15, 2005 from U.S. Appl. No. 10/131,854.
Response to Office Action dated Jun. 28, 2005 from U.S. Appl. No. 10/131,854.
Response to Office Action dated Feb. 22, 2006 from U.S. Appl. No. 10/131,854.
Response to Office Action dated Mar. 22, 2007 from U.S. Appl. No. 10/131,854.
Response to Office Action dated Jul. 9, 2007 from co-pending U.S. Appl. No. 10/798,857.
Response to Office Action dated Oct. 31, 2007 from co-pending U.S. Appl. No. 10/798,857.
Response to Office Action dated Dec. 11, 2008 from co-pending U.S. Appl. No. 10/798,857.
Response to Office Action dated Sep. 21, 2009 from co-pending U.S. Appl. No. 10/798,857.
Response to Office Action dated Jul. 1, 2010 from co-pending U.S. Appl. No. 10/798,857.
Response to Office Action dated Nov. 16, 2009 from co-pending U.S. Appl. No. 11/837,559.
Response to Office Action dated Sep. 14, 2010 from co-pending U.S. Appl. No. 11/837,559.
Response to Office Action dated Nov. 30, 2009 from abandoned U.S. Appl. No. 11/837,561.
Response to Office Action dated Sep. 16, 2010 from co-pending U.S. Appl. No. 11/837,564.
Response to Office Action dated Feb. 24, 2011 from co-pending U.S. Appl. No. 11/837,564.
Response to Office Action dated Jan. 8, 2010 from co-pending U.S. Appl. No. 11/837,565.
Response to Office Action dated Oct. 1, 2010 from co-pending U.S. Appl. No. 11/837,565.
Response to Office Action dated Mar. 21, 2011 from co-pending U.S. Appl. No. 11/837,565.
Response to Office Action dated Sep. 20, 2010 from co-pending U.S. Appl. No. 11/837,581.
Response to Office Action dated Apr. 30, 2010 from co-pending U.S. Appl. No. 11/837,600.
Response to Office Action dated Nov. 22, 2010 from co-pending U.S. Appl. No. 11/837,600.
Response to Office Action dated Jan. 11, 2010 from co-pending U.S. Appl. No. 11/837,613.
Response to Office Action dated Sep. 7, 2010 from co-pending U.S. Appl. No. 11/837,613.
Response to Office Action dated Sep. 3, 2010 from co-pending U.S. Appl. No. 11/837,620.
Response to Office Action dated Jan. 19, 2010 from co-pending U.S. Appl. No. 11/837,651.
Response to Office Action dated Sep. 7, 2010 from co-pending U.S. Appl. No. 11/837,651.
Response to Office Action dated Jan. 20, 2010 from co-pending U.S. Appl. No. 11/837,656.
Response to Office Action dated Apr. 29, 2010 from co-pending U.S. Appl. No. 11/837,656.
Response to Office Action dated Oct. 14, 2010 from co-pending U.S. Appl. No. 11/837,656.
Response to Office Action dated Mar. 16, 2011 from co-pending U.S. Appl. No. 11/837,656.
Office Action dated Aug. 31, 2011 from co-pending U.S. Appl. No. 11/837,581.
Response to Office Action dated Jun. 10, 2011 from co-pending U.S. Appl. No. 11/837,564.
Response to Office Action dated Jun. 13, 2011 from co-pending U.S. Appl. No. 11/837,581.
Response to Office Action dated May 23, 2011 from co-pending U.S. Appl. No. 11/837,613.
Response to Office Action dated May 23, 2011 from co-pending U.S. Appl. No. 11/837,620.
Response to Office action dated Aug. 1, 2011 from co-pending U.S. Appl. No. 11/837,656.
Office Action dated Sep. 15, 2011 from co-pending U.S. Appl. No. 11/837,564.
"How Many Species of Bacteria Are There?" wiseGEEK.com, accessed from Internet Sep. 23, 2011.
"Mammal," Wikipedia.com, accessed from Internet Sep. 22, 2011.
"Viruses," Wikipedia.com, accessed from Internet Apr. 18, 2012.
U.S. Office Action dated Nov. 29, 2012 from co-pending U.S. Appl. No. 11/837,559.
U.S. Office Action dated May 24, 2012 from abandoned U.S. Appl. No. 11/837,564.
U.S. Office Action dated Nov. 30, 2012 from co-pending U.S. Appl. No. 11/837,565.
U.S. Notice of Allowance dated Jun. 15, 2012 from U.S. Appl. No. 11/837,656.
U.S. Notice of Allowance dated May 11, 2012 from U.S. Appl. No. 13/108,959.
U.S. Office Action dated Sep. 24, 2012 from co-pending U.S. Appl. No. 13/572,649.
Response to U.S. Office Action dated Apr. 5, 2012 from U.S. Appl. No. 13/108,959.
Response to U.S. Office Action dated Dec. 23, 2012 from co-pending U.S. Appl. No. 13/572,649.
Sommer et al., "Minimal homology requirements for PCR primers," Nucleic Acids Research, 1989, vol. 17, No. 16, p. 6749.
Office Action dated Apr. 11, 2013 from co-pending U.S. Appl. No. 13/572,649.
Office Action dated May 7, 2013 from co-pending U.S. Appl. No. 11/837,613.
Response dated Feb. 1, 2013 from co-pending U.S. Appl. No. 13/572,649.

\* cited by examiner

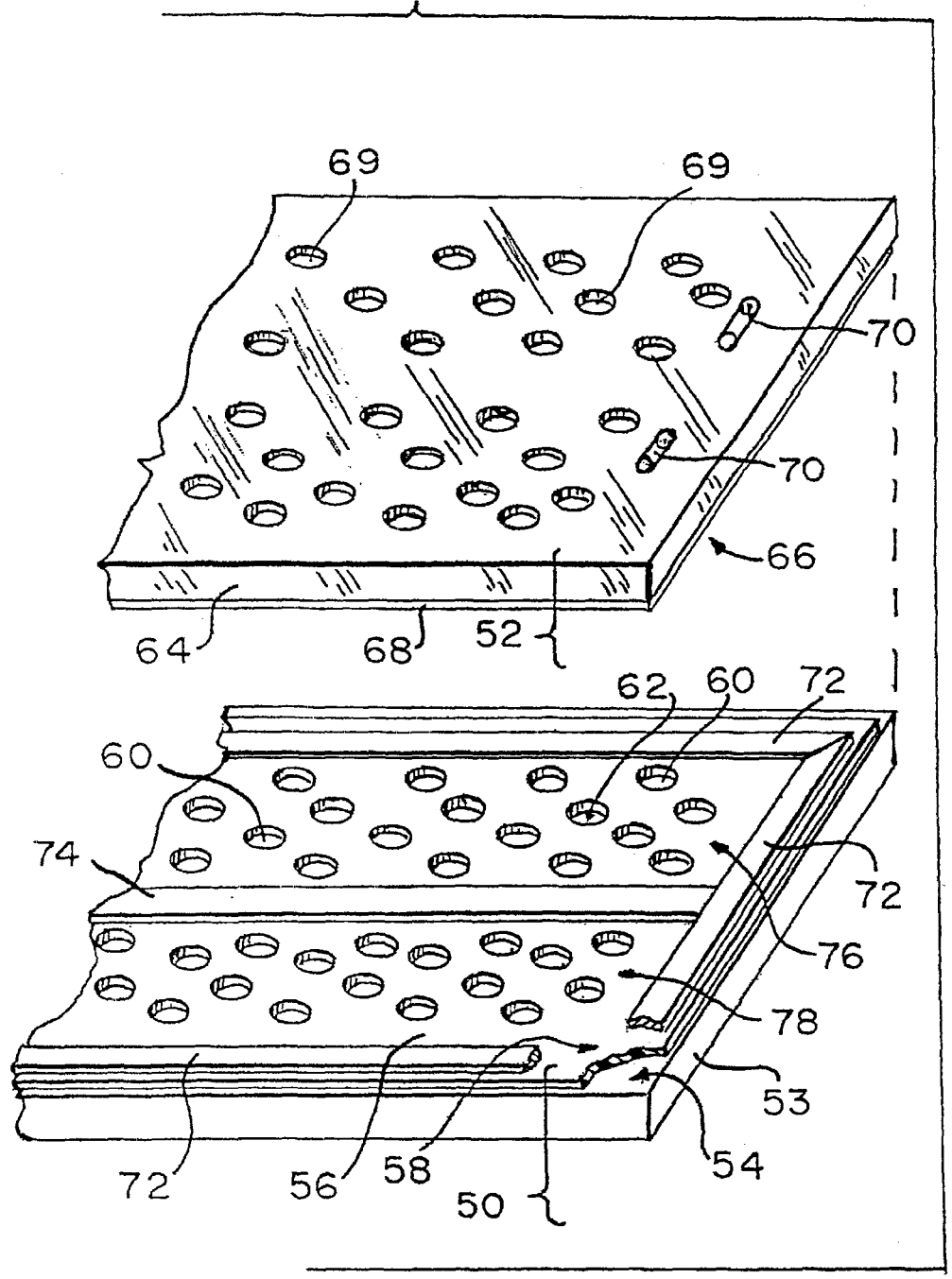

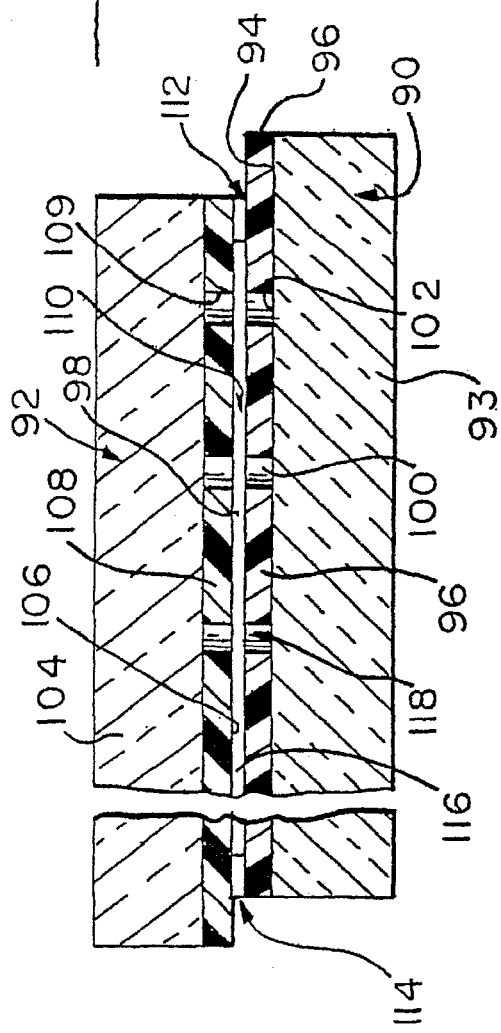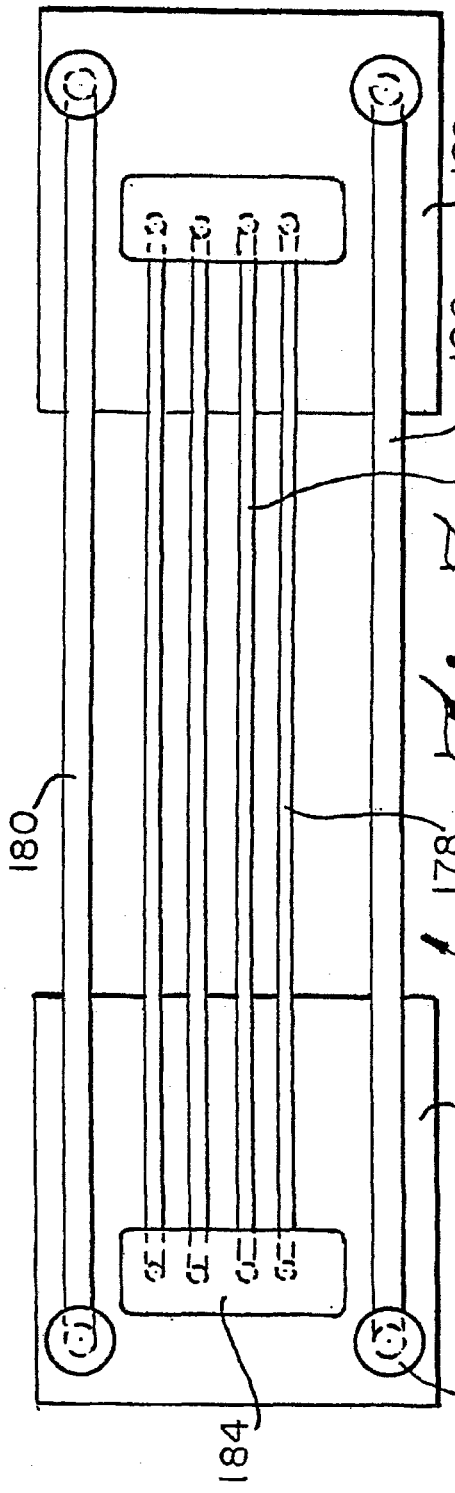

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial
<220> FEATURE:
<223> OTHER INFORMATION: Polymerase Chain Reaction Primer for the Human
      Beta Actin Gene.

<400> SEQUENCE: 1
tcacccacac tgtgcccatc tacga                                           25

<210> SEQ ID NO 2
<211> LENGTH: 25
<212> TYPE: DNA
<213> ORGANISM: Artificial
```

```
<220> FEATURE:
<223> OTHER INFORMATION: Polymerase Chain Reaction Primer for the Human
      Beta Actin Gene.

<400> SEQUENCE: 2
cagcggaacc gctcattgcc aatgg                                              25

<210> SEQ ID NO 3
<211> LENGTH: 25
<212> TYPE: DNA
<213> ORGANISM: Artificial
<220> FEATURE:
<223> OTHER INFORMATION: Dual Fluor-Labeled Probe.
<220> FEATURE:
<221> NAME/KEY: misc_feature
<222> LOCATION: (1)..(1)
<223> OTHER INFORMATION: N here denotes an A nucleotide that is labeled
      with 6-carboxyfluorescein.
<220> FEATURE:
<221> NAME/KEY: misc_feature
<222> LOCATION: (7)..(7)
<223> OTHER INFORMATION: N here denotes a C nucleotide that is labeled
      with 6-carboxytetramethylrhodamine.

<400> SEQUENCE: 3
ntgcccnccc catgccatcc tgcgt                                              25
```

METHOD OF LOADING SAMPLE INTO A MICROFLUIDIC DEVICE

CROSS-REFERENCE TO RELATED APPLICATIONS

This application is a continuation application of U.S. patent application Ser. No. 10/798,857 (the entirety of which is incorporated herein by reference), filed on Mar. 11, 2004, which is a divisional application of U.S. patent application Ser. No. 10/131,854, filed on Apr. 25, 2002, which is a divisional application of U.S. patent application Ser. No. 09/563,714, filed on May 2, 2000 (now U.S. Pat. No. 6,391,559), which is a divisional application of U.S. patent application Ser. No. 08/838,262, filed Apr. 17, 1997 (now U.S. Pat. No. 6,143,496).

This application is also a continuation application of U.S. patent application Ser. No. 10/131,854 (the entirety of which is incorporated herein by reference), filed on Apr. 25, 2002, which is a divisional application of U.S. patent application Ser. No. 09/563,714, filed on May 2, 2000 (now U.S. Pat. No. 6,391,559), which is a divisional application of U.S. patent application Ser. No. 08/838,262, filed Apr. 17, 1997 (now U.S. Pat. No. 6,143,496).

GOVERNMENT RIGHTS

Part of the work leading to this invention was carried out with the United States Government support provided under the National Institutes of Health CRADA contract No. A1000079. Therefore, the United States Government has certain rights in and to the present invention

FIELD OF THE INVENTION

The present invention relates to the in vitro amplification of a segment of nucleic acid, methods to analyze concentrations of specific nucleic acids in sample fluids, and methods for detecting amplification of a target nucleic acid sequence. The present invention also relates to miniaturized analytical assemblies and methods of filling miniaturized analytical assemblies.

BACKGROUND OF THE INVENTION

Nucleic acid amplification techniques such as polymerase chain reaction (PCR), ligase chain reaction (LCR), strand displacement amplification (SDA), and self-sustained sequence replication (3SR) have had a major impact on molecular biology research. In particular, PCR, although a relatively new technology, has found extensive application in various fields including the diagnosis of genetic disorders, the detection of nucleic acid sequences of pathogenic organisms in clinical samples, the genetic identification of forensic samples, and the analysis of mutations in activated oncogenes. In addition, PCR amplification is being used to carry out a variety of tasks in molecular cloning and analysis of DNA. These tasks include the generation of specific sequences of DNA for cloning or use as probes, the detection of segments of DNA for genetic mapping, the detection and analysis of expressed sequences by amplification of particular segments of cDNA, the generation of libraries of cDNA from small amounts of mRNA, the generation of large amounts of DNA for sequencing, the analysis of mutations, and for chromosome crawling. During the next few years, PCR, other amplification methods, and related technologies are likely to find increasing application in many other aspects of molecular biology.

Unfortunately, problems exist in the application of PCR to clinical diagnostics. Development has been slow due in part to: labor intensive methods for detecting PCR product; susceptibility of PCR to carryover contamination—false positives due to contamination of a sample with molecules amplified in a previous PCR; and difficulty using PCR to quantitate the number of target nucleic acid molecules in a sample. A need exists for a simple method of quantitative analysis of target nucleic acid molecules in a sample.

Recently, significant progress has been made in overcoming some of the problems of clinical diagnostic nucleic acid amplification through the development of automatable assays for amplified product that do not require that the reaction vessel be opened, thereby minimizing the risk of carryover contamination. Most of these assays rely on changes in fluorescent light emission consequent to hybridization of a fluorescent probe or probes to amplified nucleic acid. One such assay involves the hybridization of two probes to adjacent positions on the target nucleic acid. The probes are labeled with different fluors with the property that energy transfer from one fluor stimulates emissions from the other when they are brought together by hybridization to adjacent sites on the target molecule.

Another assay, which is commercially available is the "TaqMan" fluorescence energy transfer assay and kit, available from Perkin Elmer, Applied Biosystems Division, Foster City, Calif. This type of assay is disclosed in the publication of Holland et al., *Detection of specific polymerase chain reaction product by utilizing the 5'→3' exonuclease activity of Thermus acuaticus DNA polymerase*, Proc. Natl. Acad. Sci. USA, Vol. 88, pp. 7276-7280, August 1991, and in the publication of Livak et al., *Oligonucleotides with Fluorescent Dyes at Opposite Ends Provide a Quenched Probe System Useful for Detecting PCR Product and Nucleic Acid Hybridization*, PCR Methods and Applic., 4, pp. 357-362 (1995). The "TaqMan" or 5' exonuclease assay uses a single nucleic acid probe complementary to the amplified DNA and labeled with two fluors, one of which quenches the other. If PCR product is made, the probe becomes susceptible to degradation via an exonuclease activity of Taq polymerase that is specific for DNA hybridized to template ("TaqMan" activity). Nucleolytic degradation allows the two fluors to separate in solution which reduces quenching and increases the intensity of emitted light of a certain wavelength. Because these assays involve fluorescence measurements that can be performed without opening the amplification vessel, the risk of carryover contamination is greatly reduced. Furthermore, the assays are not labor intensive and are easily automated.

The TaqMan and related assays have provided new ways of quantitating target nucleic acids. Early methods for quantitation relied on setting up amplification reactions with known numbers of target nucleic acid molecules and comparing the amount of product generated from these control reactions to that generated from an unknown sample, as reviewed in the publication by Sninsky et al. *The application of quantitative polymerase chain reaction to therapeutic monitoring*, AIDS 7 (SUPPL. 2), PP. S29-S33 (1993). Later versions of this method used an "internal control", i.e., a target nucleic acid added to the amplification reaction that should amplify at the same rate as the unknown but which could be distinguished from it by virtue of a small sequence difference, for example, a small insertion or deletion or a change that led to the gain or loss of a restriction site or reactivity with a special hybridization probe, as disclosed in the publication by Becker-Andre, et al., *Absolute mRNA quantification using the polymerase chain reaction (PCR). A novel approach by a PCR aided transcript titration assay (PATTY)*, Nucleic Acids Res., Vol. 17, No. 22, pp. 9437-9446 (1989), and in the publication of Gilliland et al., *Analysis of cytokine mRNA and DNA: Detection and quantitation by competitive polymerase chain reaction*, Proc. Natl. Acad. Sci. USA, Vol. 87, pp. 2725-2729 (1990). These methods have the disadvantage that slight differences in amplification efficiency between the control and experimental nucleic acids can lead to large differences in the amounts of their products after the million-fold amplification characteristic of PCR and related technologies, and it is difficult to determine relative amplification rates accurately.

Newer quantitative PCR methods use the number of cycles needed to reach a threshold amount of PCR product as a measure of the initial concentration of target nucleic acid, with DNA dyes such as ethidium bromide or SYBR™ Green I, or "TaqMan" or related fluorescence assays used to follow the amount of PCR product accumulated in real time. Measurements using ethidium bromide are disclosed in the publication of Higuchi et al., *Simultaneous Amplification and Detection of Specific DNA Sequences*, BIO/TECHNOLOGY, Vol. 10, pp. 413-417 (1992). "TaqMan" assays used to follow the amount of PCR product accumulated in real time are disclosed in the publication of Heid et al., *Real Time Quantitative PCR*, Genome Research, Vol. 6, pp. 986-994 (1996), and in the publication of Gibson et al., *A Novel Method for Real Time quantitative RT-PCR*, Genome Research, Vol. 6, pp. 995-1001 (1996). However, these assays also require assumptions about relative amplification efficiency in different samples during the exponential phase of PCR.

An alternative method of quantitation is to determine the smallest amount of sample that yields PCR product, relying on the fact that PCR can detect a single template molecule. Knowing the average volume of sample or sample dilution that contains a single target molecule, one can calculate the concentration of such molecules in the starting sample. However, to accumulate detectable amounts of product from a single starting template molecule usually requires that two or more sequential PCRs have to be performed, often using nested sets of primers, and this accentuates problems with carryover contamination.

Careful consideration of the factors affecting sensitivity to detect single starting molecules suggests that decreasing the volume of the amplification reaction might improve sensitivity. For example, the "TaqMan" assay requires near saturating amounts of PCR product to detect enhanced fluorescence. PCRs normally saturate at about $10^{11}$ product molecules/microliter (molecules/µl) due in part to rapid reannealing of product strands. To reach this concentration of product after 30 cycles in a 10 µl PCR requires at least $10^3$ starting template molecules ($10^3 \times 2^{30}/10$ µl $\approx 10^{11}$/µl). Somewhat less than this number of starting molecules can be detected by increasing the number of cycles, and in special circumstances even single starting molecules may be detectable as described in the publication of Gerard et al., *A Rapid and quantitative Assay to Estimate Gene Transfer into Retrovirally Transduced Hematopoietic Stem/Progenitor Cells Using a 96-Well Format PCR and Fluorescent Detection System Universal for MMLV-Based Proviruses*, Human Gene Therapy, Vol. 7, pp. 343-354 (1996). However, this strategy usually fails before getting to the limit of detecting single starting molecules due to the appearance of artifactual, amplicons derived from the primers (so called "primer-dimers") which interfere with amplification of the desired product.

If the volume of the PCR were reduced 1000-fold to ~10 nanoliters (nl), then a single round of 30 cycles of PCR might suffice to generate the saturating concentration of product needed for detection by the TaqMan assay, i.e. $1 \times 2^{30}$ per 10 nanoliters $\approx 10^{11}$ per microliter. Attempts have been made to miniaturize PCR assemblies but no one has developed a cost-effective PCR assembly which can carry out PCR in a nanoliter-sized sample. Part of the problem with miniaturization is that evaporation occurs very rapidly with small sample volumes, and this problem is made worse by the need to heat samples to ~90° C. during thermocycling.

In addition to potential advantages stemming from ability to detect single target nucleic acid molecules, miniaturization might also facilitate the performance of multiple different amplification reactions on the same sample. In many situations it would be desirable to test for the presence of multiple target nucleic acid sequences in a starting sample. For example, it may be desirable to test for the presence of multiple different viruses, such as HIV-1, HIV-2, HIV-1, HBV and HCV in a clinical specimen; or it may be desirable to screen for the presence of any of several different sequence variants in microbial nucleic acid associated with resistance to various therapeutic drugs; or it may be desirable to screen DNA or RNA from a single individual for sequence variants associated with different mutations in the same or different genes, or for sequence variants that serve as "markers" for the inheritance of different chromosomal segments from a parent. Amplification of different nucleic acid sequences and/or detection of different sequence variants usually requires separate amplification reactions with different sets of primers and/or probes. If different primer/probe sets were positioned in an array format so that each small region of a reaction substrate performed a different amplification/detection reaction, it is possible that multiple reactions could be carried out in parallel, economizing on time, reagents, and volume of clinical specimen.

A need therefore exists for a device that can form and retain a sample volume of about 10 nanoliters or less and enable amplification to be performed without significant evaporation. A need also exists for a reliable means of detecting a single starting target nucleic acid molecule to facilitate quantification of target nucleic acid molecules. A need also exists for performing multiple different amplification and detection reactions in parallel on a single specimen and for economizing usage of reagents in the process.

SUMMARY OF THE INVENTION

According to the present invention, methods and apparatus for performing nucleic acid amplification on a miniaturized scale are provided that have the sensitivity to determine the existence of a single target nucleic acid molecule. The invention also provides analytical assemblies having sample retaining means which form, isolate and retain fluid samples having volumes of from about one microliter to about one picoliter or less. The invention also provides a method of forming fluid samples having sample volumes of from about one microliter to about one picoliter or less, and retaining the samples under conditions for thermocycling. The invention also provides an analytical assembly having means to determine simultaneously the presence in a sample of multiple different nucleic acid target molecules.

According to embodiments of the invention, PCR conditions are provided wherein a single target nucleic acid molecule is confined and amplified in a volume small enough to produce a detectable product through fluorescence microscopy. According to embodiments of the invention, samples of a few nanoliters or less can be isolated, enclosed and retained under thermocycling conditions, and a plurality of such samples can be collectively analyzed to determine the existence and initial concentration of target nucleic acid molecules and/or sequences. According to some embodiments of the invention, sample retaining chambers having volumes of about 10 picoliters or less can be achieved.

According to embodiments of the invention, methods of forming small fluid samples, isolating them and protecting them from evaporation are provided wherein different affinities of a sample retaining means and a communicating channel are used to retain sample in the means while a second fluid displaces sample from the channel. According to some embodiments of the invention, the resultant isolated samples are then subject to PCR thermal cycling.

According to embodiments of the invention, methods are provided for determining the existence and/or initial concentration of a target nucleic acid molecule in samples of about 1 microliter or less. According to some embodiments of the invention, methods are provided for a clinical diagnosis PCR analysis which can quickly and inexpensively detect a single target nucleic acid molecule.

According to some embodiments of the invention, sample chambers of about 1 microliter or less are provided that have a greater affinity for a sample to be retained than for a displacing fluid. The displacing fluid displaces sample from around the chambers and isolates the sample portion retained in the chambers.

According to embodiments of the invention, nucleic acid samples are isolated, retained and amplified in microcapillary devices having volumes of about 100 nanoliters or less, including microcapillary tubes, planar microcapillaries and linear microcapillaries. The devices may be provided with absolute, selective or partial barrier means.

According to embodiments of the invention, a porous or microporous material retains samples of about 100 nanoliters or less, and an assembly is provided which includes a cover for sealing sample within the porous or microporous material.

According to embodiments of the present invention, PCR methods and apparatus are provided wherein the sensitivity of a "TaqMan" fluorescence assay can be used to enable detection of single starting nucleic acid molecule in reaction volumes of about 100 nl or less. According to the present invention, assemblies for retaining PCR reaction volumes of about 10 nl or less are provided, wherein a single target molecule is sufficient to generate a fluorescence-detectable concentration of PCR product.

According to the invention, methods are provided for carrying out PCR in minute volumes, for example, 10 nl or less, which allows detection of PCR products generated from a single target molecule using the "TaqMan" or other fluorescence energy transfer systems.

According to embodiments of the present invention, methods of detecting and quantifying DNA segments by carrying out polymerase chain reaction in a plurality of discrete nanoliter-sized samples are provided. The present invention also provides methods for determining the number of template molecules in a sample by conducting replicate polymerase chain reactions on a set of terminally diluted or serially smaller samples and counting the number of positive polymerase chain reactions yielding specific product. The present invention is useful in detecting single starting molecules and for quantifying the concentration of a nucleic acid molecule in a sample through PCR. The present invention also provides methods of detecting and quantifying a plurality of target DNA sequences.

The present invention also provides methods and assemblies for separating and/or analyzing multiple minute portions of a sample of fluid medium that could be useful for other applications. Applications of the apparatus of the invention include the separation of biological samples into multiple minute portions for the individual analysis of each portion, and can be used in the fields of fertility, immunology, cytology, gas analysis, and pharmaceutical screening.

BRIEF DESCRIPTION OF THE DRAWINGS

The invention will be described in connection with various embodiments exemplified in the accompanying drawings, wherein:

FIG. 2 is an exploded view of an analytical assembly according to an embodiment of the present invention, shown in partial cutaway, comprising sample chambers in the form of wells formed into patterned layers on the inner surfaces of both a top plate and a bottom plate;

FIG. 3 is a cross-sectional view through a longitudinal central portion of an analytical assembly according an embodiment of the present invention;

FIG. 7 is a top plan view of a microcapillary analytical assembly according to an embodiment of the present invention;

DETAILED DESCRIPTION OF THE INVENTION

Figure 1:
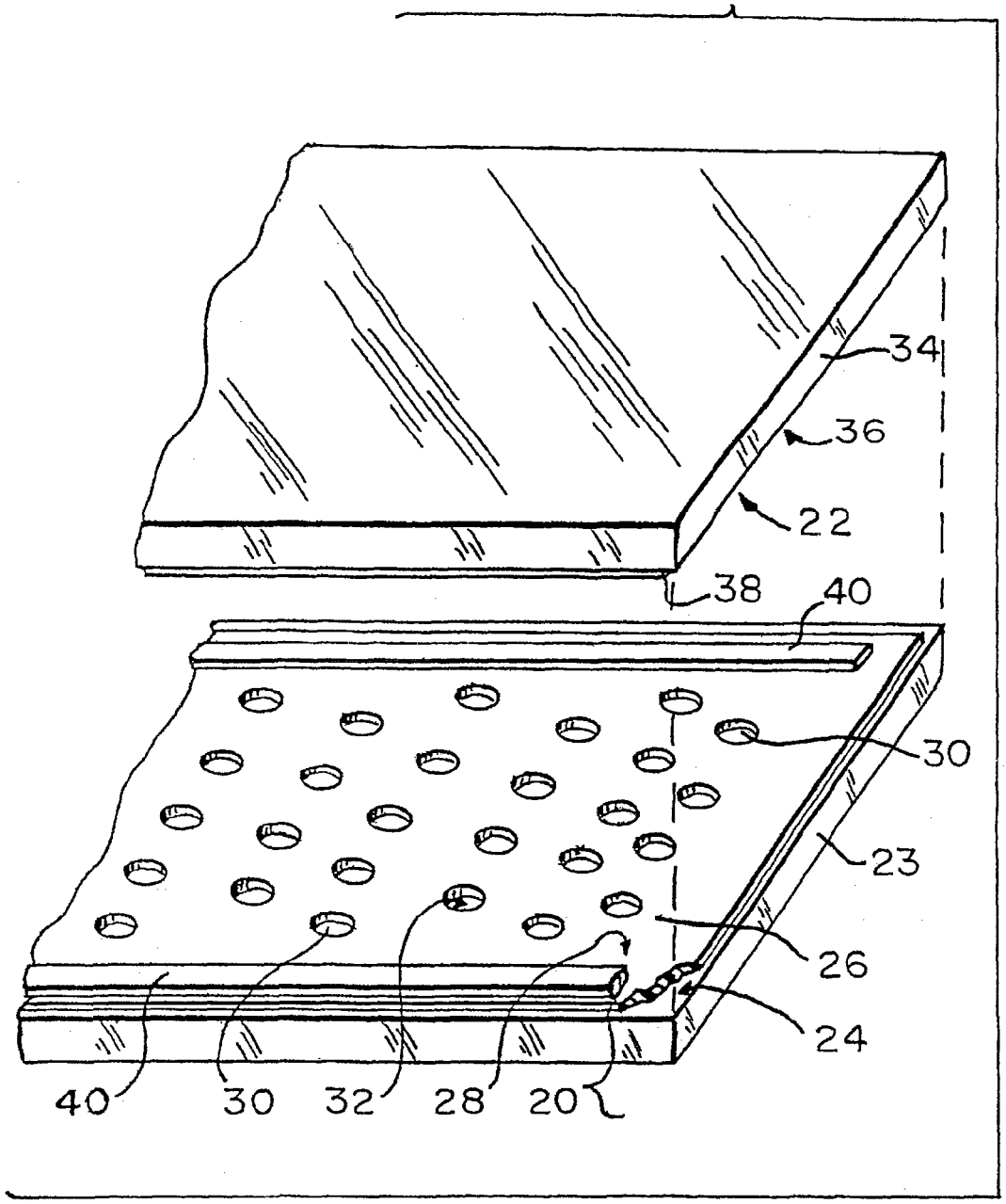
FIG. 1 is an exploded view of an analytical assembly according to an embodiment of the present invention, shown in partial cutaway.

According to embodiments of the present invention, methods of manipulating a sample of fluid medium are provided. The methods comprise loading a sample of fluid medium into sample retaining means of an analytical assembly and displacing excess sample from areas adjacent to the portion retained by the sample retaining means. According to embodiments of the invention, sample fluid is displaced from regions adjacent to the retained sample, without displacing the retained sample. In some embodiments, a displacing fluid is used to isolate a retained sample, and the displacing fluid may be curable to form a retaining chamber entrapping the fluid sample retained by the sample retaining means.

The assemblies of the present invention provide samples or sample portions enclosed in a protective environment which protects the sample or portion from evaporation and contamination. Preferably, sample is protected from evaporation at temperatures of about 95° C. or more, for example, at temperatures achieved during thermal cycling under conditions for PCR. The isolated, entrapped or enclosed sample or portion is preferably protected from contamination and evaporation throughout an amplification protocol, for example, a PCR thermal cycling protocol.

According to some embodiments of the invention, an analytical assembly is provided and comprises a plurality of sample chambers each confined in at least one dimension by opposing barriers separated by a first dimension of about 500 microns or less, preferably by 100 microns or less, and in some embodiments by about 20 microns. Means are provided for sealing the plurality of sample chambers to prevent evaporation and contamination of fluid sample confined within the plurality of sample chambers. Means are provided for restraining reaction product formed from reactions of a chemical substance restrained within the plurality of sample chambers. According to some embodiments, means may be provided for minimizing diffusion and substantially preventing convection of amplification reaction product formed from reactions of the fluid sample restrained within the plurality of sample chambers. If provided, at least one of the means for restraining and the means for minimizing diffusion and substantially preventing convection may preferably comprise a patterned layer which at least partially defines the plurality of sample chambers. Preferably, the fluid sample contains at least one target nucleic acid molecule to be amplified and constituents for enabling amplification of the target nucleic acid molecule. The fluid sample is divided into a plurality of sample portions and the plurality of sample chambers are loaded which respective portions of the fluid sample. According to some embodiments of the invention, the sample portions are in fluid communication with each other, rather than being completely isolated from each other, and separated by barrier means which may be in the shape of crosses, lines, semicircles, circles having at least one opening along the arc thereof, or other geometric shapes. According to embodiments of the invention, the barrier means may define sample retaining portions or chambers of the assembly. According to some embodiments, means for minimizing diffusion and substantially preventing convection are provided, and may comprise the herein described barrier means. According to some embodiments, the barrier means includes physical structures which may extend between the aforementioned opposing barriers which are separated by 500 microns. The barrier means may form a wall or walls between the opposing barriers. The barrier means may comprise flow restriction means. Flow restriction means may be, for example, semi-circular walls extending from one of the opposing barriers toward the other, and having the concave side of the semi-circle facing the direction of fluid flow during loading, and the semicircular arc may have at least hole or interruption therein through which air may escape during fluid sample loading. According to embodiments of the invention, the first dimension, the means for restraining, and, if provided, the means for minimizing diffusion and substantially preventing convection are such that the reaction product of a single target nucleic acid molecule amplified within at least one sample chamber can attain a concentration of reaction product molecules sufficient to be detected by a homogeneous detection assay, for example a concentration of about $10^{11}$ product molecules per microliter (μl). Preferably, at least one of the plurality of portions is initially free of the target nucleic acid molecule, and at least one of the plurality of portions initially contains at least one target nucleic acid molecule.

According to some embodiments of the invention, an analytical assembly is provided comprising a substrate and a cover in registry with one another and attached to one another and having facing surfaces spaced a substantially uniform distance apart from one another. The facing surface of the substrate comprises a first material having a first affinity to a sample of fluid to be isolated, for example, an aqieous PCR solution sample. A flow-through channel is disposed between the first material and the cover, and at least one sample retaining means is bounded on at least one side by the first material. The first material may comprise, for example, a patterned layer of moderately hydrophobic material, that is, a material having a surface energy of from about 30 dynes/cm to about 50 dynes/cm. The first material may be deposited on the inner surface of the substrate.

Herein, the term "affinity" is to be understood to mean a sample-holding capacity or sample-holding capability. The affinity of the sample retaining means may be caused by surface energy of the material contacting or restraining a sample fluid, or it may be caused by electrostatic force, flow restriction means, temperature differences or by other means. The "affinity" of a flow-through channel may be defined by the dimensions of the channel, or by the material comprising one or more bounding surface of the channel, or by a combination of dimensions and bounding surface properties. The sample retaining means may have different affinities to retain a sample fluid and a displacing fluid. The flow-through channel may exhibit different affinities to retain a sample fluid and a displacing.

According to embodiments of the invention, the first material preferably does not comprise an extremely hydrophobic material; for example, the first material preferably does not comprise a material having a surface energy of less than about 20 dynes/cm. Extremely hydrophobic materials do not tend to be wetted by aqueous samples or by many displacing fluids such as mineral oil, two-part adhesives, UV-curable and cyanoacrylate adhesives, and thus such displacing fluids would tend not to completely surround, isolate and restrain a sample (e.g. a gaseous sample) held by the sample retaining means.

The sample retaining means is in communication with the flow-through channel such that sample entering the flow-through channel can reach and be retained by the sample retaining means. The cover and first material should be of such properties and/or special relationship to allow a sample fluid and a displacing fluid to enter the flow-through channel, whether by capillary action, pressure, or other force. The sample retaining means has a second affinity to the sample of fluid medium, and the second affinity is greater than the first affinity. The second affinity may be a property induced in the first material by chemical, optical, electronic, or electromagnetic means, for example. An exemplary chemical means to permanently induce an affinity may be, for example, an $O_2$ plasma exposure to a portion of a silicone surface to effectively change the affinity of the surface to retain an aqueous sample at the portion treated. Embedding ions in a surface may also be used to permanently induce an increased or decreased affinity at a location on a surface. An affinity may be temporarily induced according to some embodiments of the invention, for example, where a surface charge on a sample retaining or repelling surface is induced to increase the effective surface tension of that surface. According to some embodiments of the invention, a temporary affinity may be reshaped, moved or relocated during or after a sample portion is retained, for the purpose of enlarging or joining sample portions in the assembly. According to embodiments of the invention, the difference of affinities enables the retaining means to collect a portion of sample from the flow-through channel and to retain the portion while a second fluid medium: is introduced to the flow-through channel; isolates sample retained by the sample retaining means; and displaces non-retained sample from adjacent to the sample retaining means.

According to embodiments of the invention, the flow-through channel is adjacent to the sample retaining means. An entrance opening is provided for introducing sample into the flow-through channel. According to embodiments of the invention, an analytical assembly is also provided which contains isolated sample entrapped by a substantially immiscible displacing fluid.

Methods according to embodiments of the invention involve causing the displacing fluid to flow through the flow-through channel and displace sample from the flow-through channel without displacing sample from the sample retaining means. Such methods are accomplished according to embodiments of the invention by providing a sample retaining means having a greater affinity for the sample than for the displacing fluid. Preferably, the flow-through channel has a much lower affinity for the sample than does the sample retaining means.

According to some embodiments of the invention, the sample of fluid medium is a gaseous sample and the sample retaining means is extremely hydrophobic, for example, having a surface energy of from about 30 dynes/cm to about 10 dynes/cm. Because of the extreme hydrophobicity of the retaining means, displacing fluids tend to be repelled from the retaining means, and thus avoid displacing gaseous sample from the retaining means. Displacing fluids can thus entrap, retain and isolate a sample within an assembly of the invention.

According to some embodiments, an organic sample is trapped in a high surface energy displacing fluid.

Both the sample to be isolated and the displacing fluid may be introduced into the flow-through channel by being drawn in under the influence of capillary forces. Pressurized loading techniques may also be used, but if displacing fluid is forced into the device under pressure, the pressure should not be so high as to displace sample from the sample retaining means. Other means of loading sample fluid and/or displacing fluid may be used according to the invention and include electrokinetic or electrostatic loading techniques, temperature differentials, centrifugal force, vacuum or suction loading, magnetic attraction loading of magnetic fluids, and electrophoretic or columbic force loading. An exemplary magnetic attraction loading technique involves drawing a fluid containing magnetic particles dispersed therein into the device under the influence of a magnetic field and using mineral oil containing dispersed iron particles as a displacing fluid and drawing the mineral oil into a flow-through channel with a magnetic field. According to some embodiments, the sample is loaded with magnetic particles and attracted toward and held by a sample retaining means adjacent to or including a source of a magnetic field or a material which is attracted to a magnet, for example, an iron-containing material.

Preferably, the displacing fluid is substantially immiscible with the sample of fluid medium to be isolated. According to embodiments of the invention wherein a displacing fluid is used, the displacing fluid may comprise a flowable, curable fluid such as a curable adhesive selected from the group consisting of: ultra-violet-curable and other light-curable adhesives; heat, two-part, or moisture activated adhesives; and cyanoacrylate adhesives. Exemplary displacing fluids include Norland optical adhesives available from Norland Products, Inc., New Brunswick, N. J., cyanoacrylate adhesives disclosed in U.S. Pat. Nos. 5,328,944 and 4,866,198, available from Loctite Corporation, Newington, Conn., resins, monomers, mineral oil, silicone oil, fluorinated oils, and other fluids which are preferably substantially non-miscible with water. According to some embodiments, the displacing fluid may be transparent, have a refractive index similar to glass, have low or no fluorescence, have a low viscosity, and/or be curable.

Some methods according to embodiments of the invention, including methods of nucleic acid molecule amplification, including PCR, may comprise isolating a sample into a plurality of discrete retained sample portions, and processing and/or analyzing the portions to determine concentrations of components and other characteristics of the sample. To carry out methods of the invention wherein a plurality of sample portions are formed and isolated, assemblies are provided having a plurality of sample retaining means. Evaluating multiple portions of a sample can then be used to determine characteristics of the entire sample.

While the resolution and accuracy of many analytical techniques can be improved according to the invention by forming and analyzing a plurality of portions of a sample, embodiments of methods of the present invention more generally involve manipulating a fluid sample. Manipulating may comprise cloning a segment of DNA, for example, where the sample of fluid medium comprises a polymerase chain reaction solution, and at least one segment of DNA to be amplified. Methods of PCR according to the invention comprise exposing isolated sample retained by the sample retaining means to a temperature profile which causes polymerase chain reaction amplification of a target nucleic acid molecule segment within the sample. According to embodiments of the invention, isolated and minute PCR samples can be retained under conditions which protect the sample during temperature profiling to dehybridize double stranded polynucleotides, anneal primers to the dehybridized molecules, and to polymerize and thus amplify the polynucleotide.

According to embodiments of the invention, PCR methods are carried out in assemblies according to the invention, and the methods include manipulating a PCR sample which contains an effective amount of a probe or system of probes having fluorescent properties or chemical properties that change upon hybridization to a nucleic acid target. According to embodiments of the invention, a normally quenched double labeled fluorescent probe is degraded upon hybridization to target DNA during PCR and the degradation results in increased emitted light of a certain wavelength. By measuring the amount of fluorescence and thus the amount of degraded probe, methods according to embodiments of the invention can be used to determine whether a segment of DNA has been amplified and thereby calculate the concentration of a target DNA segment that existed in the original sample before PCR. The measured fluorescence of a certain wavelength may in some cases be used according to the invention to quantify the amount of a DNA segment which had been retained by the sample retaining means prior to exposing a retained sample to a PCR thermal cycling profile or protocol.

Other detection methods may be used to determine PCR product and/or reactant concentrations or to make other quantitative or qualitative evaluations of many types of samples. These other detection methods include agglutination, turbidity, phosphorescence detection techniques, light scattering, light absorbance, fluorescence energy transfer, fluorescence quenching or dequenching, time-delayed fluorescence, chemiluminescence and calorimetric evaluation techniques.

According to some preferred embodiments of the invention, methods of cloning a segment of DNA are provided wherein a sample containing a DNA segment to be amplified is divided into a plurality of sample portions and the portions are simultaneously subjected to PCR. By providing sample portions of as small as about 10 nanoliters or less, for example 10 picoliters or less, single molecules of a target DNA segment to be amplified can be detected according to the invention. For PCR methods according to the invention which enable amplification of a plurality of sample portions simultaneously, the sample from which the portions are derived may comprise a polymerase chain reaction solution, at least one segment of DNA to be amplified, and a sufficient amount of primer to carry out a polymerase chain reaction for multiple cycles, and the method may comprise exposing the sample portions retained by the plurality of sample retaining means to a temperature profile which causes polymerase chain reaction and amplification of a target DNA segment within the portions. According to embodiments of the invention, the presence of a single strand of a target DNA segment can be detected in a portion retained by at least one of a plurality of sample retaining means.

Methods according to some embodiments of the present invention comprise manipulating a sample of fluid medium by loading the sample into an analytical assembly having a porous sample retaining means. Porous sample retaining means according to the invention comprise a porous structure having an exposed porous surface and a plurality of pores having open upper ends at the exposed porous surface. Preferably, the exposed porous surface is moderately hydrophobic yet receptive to adhesive bonding. The pores of the sample retaining means may have substantially the same volume and have closed lower ends which may be defined by a substrate onto which the porous structure may be disposed.

Preferably, the ratio of pore diameter to depth is from about 2:1 to about 10:1, for example, 4:1 for embodiments wherein a porous material is attached to a substrate. According to embodiments of the invention, the ratio of exposed porous surface area, that is, the area of the surface not taken up by the openings, to the area of pore openings is from about 4:1 to about 1:1.5, for example, a ratio of about 1:1.

The pores have a first affinity to a sample such that when the sample is disposed upon the exposed porous surface, the sample is drawn into the plurality of pores. The assembly used according to these methods of the invention further comprises means to displace sample from the exposed porous surface without displacing the sample from the pores. The means to displace may comprise a displacing fluid or a displacing device such as a coverslip pressed against the exposed surface. The assembly may also include means for sealing the sample within the pores to prevent evaporation and contamination of the sample during heat treatment and analysis of the sample in the pores.

Loading sample into the pores of a porous sample retaining means comprises contacting the sample to the exposed porous surface and retaining the sample in the plurality of pores. Due to the affinity the pores exhibit to the sample, particularly to aqueous PCR samples, the sample is drawn into the pores by capillary force and retained therein. The methods also include displacing sample from the exposed porous surface without displacing sample from within the pores. The methods may also include sealing the open ends of the pores with the sample disposed therein.

According to some embodiments of the invention, both the top and the bottom of the pores may be open for loading and then sealed.

According to embodiments of the invention, analytical assemblies are provided for carrying out methods of manipulating a sample of fluid medium with a porous sample retaining means.

The porous sample retaining means in such assemblies may comprise a microchannel array, a metal, glass, ceramic, cellulosic or polymeric screen or sieve, or a material having a plurality of pores formed therein, such as a substantially flat plastic disk having a plurality of pores ablated, molded, etched or drilled therein. The pores may be treated or coated with a material to provide an affinity to a sample. The exposed porous surface may be treated or coated with a material to render the exposed surface moderately hydrophobic.

According to some embodiments, the sample retaining pores have a volume of from about 1 microliter to about 100 nanoliters or less, preferably about 10 nanoliters or less, and may have pore volumes of about 1 picoliter or less for some applications. According to one embodiment, the pores have volumes of about 10 picoliters.

After sample is loaded into the pores of the porous sample retaining means, remaining sample which is not retained by the pores but rather which remains on the exposed porous surface is removed or displaced. According to embodiments of the invention, a sealing means such as a microscope slide coverslip, tape, film or a device including other components, a silicon film or device, a device having an array of reactants, or other means is disposed on the exposed porous surface and displaces sample from the exposed porous surface, without displacing sample from within the pores. After displacing sample from the exposed porous surface, the displacing means may become the sealing means if subsequently held, adhered or attached to the porous surface, which would then no longer be exposed. Preferably, the sealing means comprises a material having a second affinity for the sample which is less than the first affinity, for example, the sealing means comprises a relatively hydrophobic material which contacts the exposed porous surface, and the pores are defined by a relatively hydrophilic porous material.

According to embodiments of the invention using the aforementioned porous sample retaining means, the means for displacing sample and the means for sealing may be a single cover having a hydrophobic surface which contacts the porous surface. The sealing means may be glued to the previously exposed porous surface, glued to a substrate on which the porous retaining means is disposed, or clamped or otherwise attached to the porous retaining means or a substrate therefor, as for example, with clips or springs. A surface of the cover, substrate or porous sample retaining means may provide adhesive or glue properties.

According to methods of some embodiments of the invention, a target nucleic acid molecule or segment, is amplified in at least one of the pores of a porous sample retaining means. According to such embodiments, the sample to be retained by the retaining means may comprise a polymerase chain reaction solution, and at least one target segment of nucleic acid molecule to be amplified. The method further comprises exposing the sample sealed within the pores to a temperature profile which causes polymerase chain reaction amplification of the target segment within at least one of the pores. In some embodiments of the invention, the sample further comprises an effective amount of a fluorescent probe which fluoresces upon degradation caused by the successful amplification of the target segment in the sample. Such methods may further comprise measuring the fluorescence emitted from degraded probe after the polymerase chain reaction and determining whether the target segment was amplified in at least one of the pores. The fluorescence measurement may be of the amount of fluorescence, the lifetime of fluorescence, or another fluorescence property.

The methods of the present invention using a porous sample retaining means may further comprise using measured fluorescence to quantify the amount of target nucleic acid segment which had been retained in at least one of the pores prior to exposing retained sample portions to a thermal cycling protocol. Due to the extremely small volume of sample chambers which can be achieved with a porous sample retaining means, the presence of a single strand of the target segment can be detected in the pores. The methods may also comprise determining the initial concentration of the target segment which had been in the sample prior to amplification.

According to yet other embodiments of the present invention, methods of manipulating a sample of fluid medium are also provided wherein a sample of fluid medium is loaded into an analytical assembly comprising a microcapillary device, for example, a microcapillary tube having an inner diameter of about 500 µm or less, preferably about 100 µm or less. Loading may comprise filling the microcapillary tube with a sample by capillary action. Microcapillary devices provided with a sample retaining means, for example, a hydrophobic or hydrophilic surface or an electromagnetic or electrostatic force, may have an inner dimension or inner diameter of about 500 µm or less. Tubular or linear microcapillaries not provided with sample retaining means may preferably have an inner dimension of about 100 µm or less. Planar microcapillaries not provided with sample retaining means, for example, comprising the space between two facing plates, may preferably have an inner dimension of about 20 µm or less.

According to some embodiments, a first fluid may initially be disposed into the microcapillary device, for example, a microcapillary tube. The first fluid may preferably be substantially immiscible, and more preferably, completely immiscible with a sample fluid. Loading then comprises disposing a portion of a sample fluid into the microcapillary tube adjacent the first fluid, and subsequently disposing a second fluid into the microcapillary tube adjacent the sample. The second fluid is also preferably substantially immiscible, and more preferably completely immiscible, with the sample. The sample is disposed between and restrained by the first and second fluids. The first and second fluids may be the same fluid, and can be, for example, mineral oil or a gas or a curable monomer formulation, if the sample is an aqueous fluid. The microcapillary device may contain more than one isolated sample portion, which may be separated by one of the first and second fluids. Each portion may be about 100 nl or less, preferably 10 nl or less.

Some methods of the invention which employ microcapillary sample retaining means may also comprise sealing both ends of the microcapillary tube with the sample therein. The sample may fill the entire capillary tube and be sealed therein, or the sample may be sealed in the tube sandwiched between first and second fluids. Means may be employed to load numerous sample portions, such as an ink jet or fluidic control apparatus.

According to embodiments of the invention, microcapillary analytical assemblies are also provided and can be used to isolate and retain a sample of fluid medium comprising about 100 nanoliters or less of a fluid medium, preferably about 60 nanoliters or less. Assemblies are also provided which comprise a plurality of such microcapillary tubes, each tube having a sample of fluid medium disposed therein. A plurality of tubes may be attached to a pair of microscope slide coverslips, or to a tape or pair of tapes, or otherwise held together.

The microcapillary sample retaining devices of the present invention may be used to carry out nucleic acid amplification methods, according to embodiments of the invention. When used in PCR applications, the fluid sample may comprise a polymerase chain reaction solution which may include reagents, enzymes, buffer, bovine serum albumin and other well known ingredients commonly used to perform a polymerase chain reaction. Methods according to the invention which employ the inventive microcapillary devices may further comprise exposing the sample sealed within the microcapillary tube, or within a plurality of tubes, to a temperature profile which causes amplification of the target segment within the sealed sample.

As mentioned in connection with other methods and apparatus according to the invention, the PCR sample in the microcapillary tube may further comprise an effective amount of a fluorescent probe which fluoresces upon degradation of the probe caused by the successful amplification of the target segment. The fluorescence emitted from the hybridized probe can be measured to determine whether the target segment was amplified. By using different dilutions of starting sample or by using replicate samples in different volumes, the concentration of starting target segment can be determined.

According to embodiments of the present invention wherein PCR is carried out in a microcapillary assembly, fluorescence or other detection properties are promptly analyzed after PCR thermal cycling, for example, within about 5 hours, more preferably within about 1 hour after PCR thermal cycling is complete. Prompt analysis of the fluorescence emitted maximizes the concentration of measured degraded probe along regions of the microcapillary tube, before the degraded probe diffuses along the tube and becomes less detectable. Preferably the amplification is carried out as rapidly as possible, for example, in less than one hour.

Miniaturized assemblies according to embodiments of the invention have been briefly described above and will be discussed in greater detail below. Assemblies according to embodiments of the invention can take many forms but can generally be classified into three types, (1) assemblies having flow-through channels and sample retaining means in communication with the flow-through channel, (2) assemblies having porous sample retaining means and means for sealing sample within sample retaining pores, and (3) assemblies comprising at least one microcapillary tube.

According to embodiments of the invention, assemblies are provided for manipulating samples of fluid medium, for example, methods for isolating small sample volumes, such as sample volumes of 100 nanoliters or less.

Some assemblies according to the invention comprise a substrate and a cover in registry with and attached to one another and having facing surfaces spaced a substantially uniform distance apart from one another. The facing surface of the substrate comprises a first material having a first affinity to a sample of fluid medium to be contained in the assembly. For example, if an aqueous fluid is to be manipulated, the first material is preferably a moderately hydrophobic material. The first material preferably defines at least a portion of a flow-through channel which is disposed between the substrate and the cover. The flow-through channel is in fluid communication with a sample retaining means, and the retaining means is bounded an at least one side thereof by the first material. The sample retaining means has a second affinity to the same sample of fluid medium. Preferably, the second affinity to the sample fluid is greater than the first affinity thereto, preferably much greater, enabling the sample retaining means to retain or collect a portion of a sample of fluid medium which flows through the flow-through channel and to retain the portion while a second fluid medium flows through and displaces sample from the flow-through channel. The result can be a very small isolated portion of the sample being retained by the sample retaining means and entrapped, encased or otherwise surrounded by the second fluid medium in the flow-through channel.

According to embodiments of the invention wherein the assembly comprises a flow-through channel and sample retaining means, the substrate may be a first plate having a patterned layer of the first material formed thereon. The cover may be a second plate attached to and substantially parallel to the first plate, with the first and second plates having facing substantially parallel planar surfaces. The first and second plates may each be rigid or flexible, flat or contoured, a sheet, a film, a microscope slide, a microscope slide coverslip, a glass plate, a tape, a device including other components, a silicon device, a silicon film, or the like. According to some embodiments, the plate has a substantially planar surface on a side adjacent or defining the sample retaining means. The patterned layer is preferably located between the planar surfaces and at least partially forms a boundary for the sample retaining means. For example, when the sample retaining means is a chamber formed from an opening in, a cavity or recess in, or a hole through the patterned layer, the closed end of the chamber may be defined by the substrate surface on which the patterned layer is disposed or by the patterned layer, and the patterned layer may define the sidewalls of the sample chamber. According to embodiments wherein the sample retaining means is a recessed sample chamber at least partially defined by the patterned layer, the chamber may comprise a sidewall, a closed lower end, and an upper end which may be open or closed. The sample chamber has a communication with the flow-through channel. According to some embodiments of the invention, the sample chamber also extends into and is partially defined by a patterned layer formed on the facing surface of the assembly cover, in which case the sample chamber may have a closed upper end and the communication to the chamber may be formed in the chamber sidewall, for example, an annular gap in an otherwise continuous sidewall. According to other embodiments of the invention, the cover is substantially planar and the sample chamber does not extend into the cover or a layer disposed on the cover, in which case the chamber has an open upper end in communication with the flow-through channel.

According to embodiments of the invention wherein the substrate and cover comprise first and second plates, the closed lower end of the sample chamber may comprise the first plate. The sample retaining means may comprise a third material at the lower end of the sample chamber. The third material may in some cases be a hydrophilic material deposited on the first plate and defining the lower end of the chamber. According to some embodiments, the third material may be very hydrophobic. For aqueous samples in particular, hydrophilic materials may be used at the lower end of the sample chamber. According to some embodiments of the present invention, a sample chamber comprising a recess in a substrate or substrate coating may preferably have hydrophilic material at a lower end thereof and hydrophobic material forming the sidewall. Preferably, the hydrophilic lower end provides an affinity to an aqueous PCR sample which is sufficient to retain the sample while a displacing fluid carries away sample adjacent the sample chamber. The hydrophobic sidewalls prevent sample from being displaced from the sample chamber.

Preferred sample chambers according some embodiments of the invention, for nucleic acid amplification methods to detect single target nucleic acid molecules, have volumes of from about 1 microliter to about 1 picoliter or less. Printing, photolithography, etching, ablation and other methods of forming sample chambers in, for example, printed layers, can provide sample chambers of ten nanoliters or less, for example, about 100 picoliters.

Screen printing and photolithography are preferred methods of forming a patterned layer on the substrate. Screen printing methods can provide a patterned layer on a 1 inch by 3 inch microscope slide wherein the layer contains over one thousand isolated and spaced sample chambers each having a volume of about 1 nanoliter. Such a patterned layer could enable over one thousand PCR chambers of about 1 nanoliter each, all on the surface of a 1"×3" microscope slide. Photolithographic methods can provide from about 10,000 to over 100,000 sample chambers of about 100 picoliters each on a 1"×3" substrate.

According to embodiments of the invention, the first material or patterned layer material is moderately hydrophobic. Herein, the term "moderately hydrophobic" refers to a material or layer that exhibits a contact angle to water of from greater than about 30° to less than about 85°. According to some embodiments, a hydrophobic patterned layer is disposed on the facing surfaces of both the substrate and the cover, the average contact angle of the two patterned layers is preferably more than about 30° to less than about 85°, and more preferably each of the two layers is moderately hydrophobic. Patterned layers exhibiting higher contact angles to water may be employed on the substrate surface if the cover comprises a hydrophilic facing surface. Preferably, the patterned layer or first material is of such a nature that displacing fluid can bond thereto when the second fluid or displacing fluid is a polymerizable fluid. If the patterned layer or first material comprises TEFLON, for example, a curable or polymerizable displacing fluid may not be capable of bonding thereto and thus may not sufficiently seal an entrapped sample fluid posing contamination and evaporation risks.

According to some embodiments of the invention, the substrate and cover comprise first and second facing planar surfaces with a first layer on the first surface and a second layer on the second surface. According to some embodiments, sample chambers are formed in the first layer and the second layer is substantially smooth. According to some other embodiments, the second layer also has sample chambers formed therein, preferably mirroring the sample chambers formed in the first layer. The second layer may comprise a moderately hydrophobic material.

According to some embodiments, the interior surface(s) of the substrate and/or cover may be altered by chemical or other means to form a pattern of retaining means having altered surface energy or structure.

According to some embodiments of the invention, a sample chamber comprises a hole or recess formed in a first patterned layer, and a hole or recess formed in a second patterned layer, the sidewall comprises both the first and second patterned layers, a flow-through channel is disposed between the first and second patterned layers, and the communication to the flow-through channel interrupts the sidewall.

According to embodiments comprising first and second patterned layers, the first and second layers may comprise the same material. The second patterned layer may have a substantially smooth surface facing the first patterned layer, and the second layer may have a substantially uniform layer thickness. In embodiments wherein a smooth and continuous second layer is provided on the inner surface of a cover or top plate of an assembly, the sample chamber may have an open upper end in fluid communication with the flow-through channel and the sidewall may completely comprise the first patterned layer.

The patterned layer may be the retaining means, for example, hydrophobic or hydrophilic spots on the substrate or cover. According to some embodiments, the patterned layer may comprise the retaining means and may comprise a microporous material such as an epoxy material which is highly filled with micron-sized beads.

According to embodiments of the invention wherein an assembly comprises a flow-through channel, the flow-through channel may have an entrance opening and an exit vent. Assemblies designed for forced pressure loading may not require an exit vent. In embodiments of the invention comprising a flow-through channel, the channel may have a substantially uniform cross-sectioned area throughout. In other embodiments, the cross-sectional area of the flow through channel increases or decreases in a direction from the entrance opening to said exit vent. The changing cross-sectional area of the flow-through channel can influence the travel of the sample and/or displacing fluid through the flow-through channel due to increasing or decreasing resistance of the fluid flow. For example, in embodiments wherein the flow-through channel increases in cross-sectional area from adjacent to the entrance opening in the direction of the exit vent, fluid flow toward the exit vent is subject to decreased flow resistance compared to embodiments wherein the cross-sectional area is the same throughout the flow-through channel. One method of forming a flow-through channel with an increasing or decreasing cross-sectional area is to space the cover or top plate further from the substrate or bottom plate at the entrance end of the assembly than at the exit end. Although the substrate and cover, or first and second plates, would remain substantially parallel to each other as defined by the present invention, they would not be exactly parallel. Another method of forming an increasing or decreasing flow-through channel cross-sectional area is to form the patterned layer thicker at one end of the device than at the opposite end of the device, and to have the thickness of the layer gradually increase or decrease in thickness. According to some embodiments wherein holes in a patterned layer define sample retaining means, the retaining means may have different sizes and shapes.

According to some embodiments of the invention, a hydrophilic pattern is provided to form sample retaining means and the pattern may be induced by electrets or by internal or external electrodes to provide a charged surface having higher surface energy and wettability than a flow-through channel in communication with the retaining means.

According to some preferred embodiments of the invention, an analytical assembly is provided with a plurality of sample retaining means separated from one another. In some embodiments, the plurality of sample retaining means comprise sample chambers formed in a patterned layer disposed between the substrate and cover or first and second plates. The sample retaining means may comprise chambers each having a sidewall, an upper end, a closed lower end, and a communication with a flow-through channel.

Filled assemblies are also provided according to embodiments of the invention, and may comprise a sample fluid retained by the sample retaining means, and a different, second fluid retained in the flow-through channel. Preferably, the second fluid is substantially immiscible with the sample fluid. The sample fluid may comprise a polymerase chain reaction solution and at least one segment of DNA to be amplified. The second fluid is referred to as a displacing fluid and may comprise a curable fluid, particularly curable adhesives, and preferably fluid adhesives selected from the group consisting of light-curable, heat-curable, two-part-curable, moisture-curable and cyanoacrylate adhesives. When UV-curable adhesives are used and cured, UV-blocking spots may be provided on the cover and/or substrate, aligned with the sample retaining means, to protect the retained sample from harmful light.

According to some embodiments of the invention, wherein an assembly is provided having opposing surfaces, sample retaining means between the surfaces, and a flow-through channel in communication with the retaining means, the sample retaining means may comprise a fibrous or porous material which absorbs a sample of fluid medium through capillary forces. The fibrous or porous material may be formed on a patterned layer of a first material deposited on one of the surfaces. The first material may comprise a moderately hydrophobic material. A second material layer may be included on one of the facing surfaces and may comprise a moderately hydrophobic material. The fibrous or porous material may be a cellulosic material, a filter paper material, absorbent textured material, absorbent sintered materials, absorbent pastes, microporous membranes, fiberglass, and the like. Preferably, the fibrous or porous material is a porous membrane having a maximum pore diameter size of about 1 micron. The fibrous or porous material may fill the gap between the substrate and cover or may be disposed on just one of the interior substrate or cover surfaces.

The fibrous or porous material has a wicking rate for a sample which can be measured in millimeters per second, and sample flowing through the flow-through channel advances through the channel at an advancing rate which can be measured in millimeters per second. Preferably, the wicking rate exceeds the advancing rate, thus minimizing the possibility of an aqueous sample entrapping or encircling the sample retaining means before air in the retaining means can escape and be carried away by the advancing fluid. In cases where the advancing rate exceeds the wicking rate, sample tends to be absorbed too slowly by the retaining means and the advancing fluid in the channel tends to surround the retaining means and entrap air before the air has a chance to escape.

The size and shape of the porous retaining means also influences whether air will be trapped in the sample retaining means. For larger sample retaining means, there is a greater chance that air may be entrapped in the sample retaining means than for smaller sample retaining means. Therefore, it is preferable to use higher wicking rates for larger fibrous or porous sample retaining means than for smaller retaining means. For example, if the retaining means has a wicking rate of 1 mm/sec and the advancing rate is also 1 mm/sec, a substantially flat sample retaining means having a diameter of about 1 mm tends to be wicked by sample without entrapping air, whereas a retaining means having a diameter of about 2 mm may not be completely wicked with sample but instead is more likely to entrap air. Retaining means that are elongated in the direction of sample flow may be preferred for large samples.

According to some embodiments of the invention, sample retaining means are provided which exhibit an affinity to retain a sample through application of a generated force. Rather than using materials having different affinities, the sample retaining means may be provided with means to generate, for example, an electrostatic force. Indium oxide or other conductive coating materials can be strategically placed on or in the substrate, cover or patterned material to form a region or spot which can be charged to form an electrostatic attractive force. If a curable displacing fluid is then used to displace sample from around the charged region or spot, generation of the force is no longer needed after the displacing fluid displaces sample and/or cures.

In some embodiments wherein a generated force is used to retain sample in a region or at a spot, the generated force may be a temperature gradient or temperature altering means which provides a temperature to the sample retaining means which affects the affinity of the retaining means to a sample, and produces a different affinity for the sample at the retaining means than at surrounding regions of the assembly such as in the flow-through channel.

According to some embodiments of the invention having a flow-through channel, the sample retaining means is not a sample well or recess but rather a sample chamber formed between a patch of a second material and a cover or patch of a third material. The second and third materials may be the same, and preferably both the second and third materials have a greater affinity for a sample of fluid medium than a first material layer which at least partially defines the flow-through channel. For example, the second and third materials preferably have a greater affinity for an aqueous PCR sample than the affinity the first material exhibits to the same PCR sample. According to some embodiments, the patch or spot of the second and/or third material is disposed on the first material.

According to embodiments of the invention having a flow-through channel, the substrate is a first plate having a patterned layer formed thereon, and the cover is a second plate attached to and substantially parallel to the first plate. The first and second plates have facing substantially parallel planar surfaces, and the patterned layer is located between the planar surfaces and at least partially bounds the sample retaining means. The sample retaining means comprises a sample retaining patch disposed on the patterned layer and is spaced a first distance from the facing surface of the second plate. Preferably, the flow-through channel has a bottom surface which is spaced from the facing surface of the second plate by a second distance, and the second distance is greater than the first distance. According to some preferred embodiments, the sample retaining means comprises a plurality of sample retaining patches disposed on the patterned layer, spaced from one another, and spaced a first distance from the facing surface of the second plate.

According to some embodiments of the invention, the substrate comprises a flexible material, for example, a polymeric film such as polypropylene film, polyethylene film, polycarbonate film, polyethyleneterephthalate film, silicone film, teflon film, celluloid film, or other film such as a metal or ceramic film. When a flexible material is used, it may instead be molded or formed if not in the form of a tape. The cover may also comprise a flexible material such as a polymeric film, such that the entire assembly is substantially flexible. According to such embodiments, a flexible tape can be constructed and cut to size depending upon the number of sample retaining means desired to be utilized. An entrance opening and an exit vent can be used to load and displace sample fluid, and to load displacing fluid. The entrance opening and/or exit vent may be in the form of a gap formed between the substrate and cover at an end or gaps formed at opposite ends of a piece of tape and in communication with a flow-through channel and a supply of sample to be apportioned.

According to embodiments of the invention, a combination is provided which includes a miniaturized assembly for containing a sample of fluid medium, a means for displacing a portion of a sample of fluid medium, and a sealing means, which may be packaged together as a kit, or available separately. The miniaturized assembly comprises a substrate having a surface and a sample retaining means disposed on the surface. The sample retaining means comprises a porous structure having a porous surface and a plurality of pores having open ends at the surface. The pores may each have substantially the same volume and closed lower ends. The pores have a first affinity to a sample of fluid medium such that a sample of fluid medium disposed upon the porous surface is drawn into and retained by the plurality of pores. The pores preferably have an affinity to retain a sample of aqueous medium, particularly an aqueous PCR sample. The means to displace a sample of fluid medium from the porous surface without displacing the sample from within said pores may comprise a cover or coverslip, for example, a standard microscope slide coverslip. Preferably, the cover or coverslip has a hydrophobic surface, which may be adhesive, and which contacts the porous surface and is not wet by aqueous samples. The cover or coverslip may be permanently attached to the substrate after displacing sample from the porous surface, or the cover or coverslip may be removed and replaced with a sealing device. The sealing device according to this and other embodiments is preferably transparent so that fluorescence emitted from sample retained by the sample retaining means can be observed and/or measured. The means for displacing fluid and the means for sealing are the same device, for example, a single covering device such as a single coated microscope coverslip. The porous sample retaining means may be a metal plastic, glass or ceramic sieve or screen, or other materials having a plurality of pores formed therein, such as a substantially flat plastic disk having a plurality of pores etched, ablated, molded, drilled, poked or otherwise formed therein. The volume of the pores may be from about 1 microliter to about 1 picoliter or less. Preferably, the volume of the pores is about 100 nanoliters or less, and for some applications may be 1 nanoliter or less.

According to some embodiments of the invention, an analytical assembly is provided comprising a microcapillary tube having opposite ends, an inner diameter of about 100 microns or less, and at least one amplifiable nucleic acid molecule segment entrapped inside the tube. Microcapillary tubes having inner diameters of about 500 µm or less may also be used if a sample restraining means is included in the tube, for example, glass beads, gels, absorbent particles, barrier means or electrophoretic means. Tube lengths of from about 1 mm to about 100 mm are preferred.

Capillary action is preferably used to introduce a sample fluid in the microcapillary tube, and after the sample is disposed in the tube, the tube is sealed at both ends thereof to entrap the sample inside. The sample may be divided into a plurality of portions separated by, for example, mineral oil. The entrapped sample or sample portions is/are thereby protected from contamination and from evaporation. The sample of fluid medium disposed in the tube may have a volume of about 100 nanoliters or less, more preferably about 10 nanoliters or less, and for some applications, a volume of about 1 nanoliter or less.

According to some microcapillary embodiments, a first fluid is disposed in the tube on a side of the sample and adjacent to the sample, and the first fluid is preferably substantially immiscible with the sample. A second fluid may be disposed in the tube on the opposite side of the sample and adjacent to the sample, and the second fluid is also preferably substantially immiscible with the sample, such that the sample is disposed between, and restrained by, the first and second fluids. According to some embodiments, the sample is an aqueous medium and the first and second fluids are both mineral oil or polymerizable fluid. According to some embodiments, the sample preferably comprises about 100 nanoliters or less of a fluid medium. Multiple isolated sample segments may be introduced by ink jet or other sample dispensing means.

The microcapillary assemblies according to embodiments of the invention may comprise a plurality of sealed microcapillary tubes having inner diameters of 100 microns or less, with each tube containing at least one portion of a sample of fluid medium. Microcapillary tubes having inner diameters of about 500 μm or less may also be used if a restraining means such as a mineral oil is used to separate minute sample portions from each other. Tube lengths of from about 1 mm to about 100 mm are preferred. The tubes may each contain substantially immiscible fluids on opposite sides of the respective portion(s) of sample within each tube, such that the sample portion(s) in each tube is/are disposed between, and restrained by, the substantially immiscible fluid. The substantially immiscible fluids are preferably essentially immiscible with the sample. According to some embodiments, the sample comprises a polymerase chain reaction solution including primer, and at least one segment of a nucleic acid molecule to be amplified.

According to embodiments wherein microcapillary assemblies are provided, the tube or tubes used in the assembly may be self sealing or sealed at either or both ends thereof with a curable fluid, preferably a curable adhesive. Exemplary curable adhesives include those selected from the group consisting of light-curable, heat-curable, two-part-curable, moisture-curable and cyanoacrylate adhesives. When UV-curable adhesives are used and cured, UV-blocking spots may be provided on the cover and/or substrate, aligned with the sample retaining means, to protect the retained sample from harmful light.

According to yet other embodiments of the invention, a method is provided for loading a fluid sample into an assembly for isolating and retaining a small portion of the sample. Assemblies for carrying out such methods comprise a sample retaining means, for example, sample chambers, for retaining the small portion of the sample. The method of loading a fluid into an assembly may comprise providing a first fluid to be retained and providing a displacing fluid. An assembly is provided comprising a substrate and a cover having facing surfaces spaced from one another, wherein the facing surface of at least one of the substrate and the cover comprises a first material. The assembly has a flow-through channel between the substrate and the cover, and a first fluid retaining means bounded on at least one side thereof by the first material. The channel is in communication with the flow-through channel. The first fluid retaining means has a first affinity to the first fluid and a second affinity to the displacing fluid, and the flow-through channel has a third affinity to the first fluid and a fourth affinity to the displacing fluid. The first, second, third and fourth affinities are such that the first fluid retaining means retains at least a portion of the first fluid loaded into the assembly while displacing fluid displaces first fluid from the flow-through channel. The displacing fluid preferably can displace the first fluid from the flow-through channel without substantially displacing first fluid from the first fluid retaining means. The method further comprises causing the first fluid to be loaded into the flow-through channel and be retained by the first fluid retaining means, and causing the displacing fluid to enter the flow-through channel and displace first fluid from the flow-through channel without substantially displacing first fluid from the first fluid retaining means. According to some embodiments of the invention, the first affinity is greater than the second affinity. According to some embodiments, the fourth affinity is greater than the third affinity. According to some embodiments, the flow-through channel comprises at least one bounding surface and has dimensions, and the third and fourth affinities are provided by the dimensions of the flow-through channel and the respective affinities of the at least one bounding surface to the first fluid and to the displacing fluid.

According to some embodiments of the invention, a method is provided which comprises providing an assembly including a substrate and a cover in registry with and attached or affixed to one another and having facing surfaces spaced a substantially uniform distance apart from one another. The facing surface of the substrate comprises a first material having a first affinity to a sample of fluid medium to be contained in the assembly. A flow-through channel is disposed between the substrate and the cover, and the sample retaining means is bounded on at least one side thereof by the first material. The first material may be, for example, a surface of a glass plate or slide, or a patterned layer such as a hydrophobic material layer deposited on the facing surface of the substrate. The sample retaining means is in communication with the flow-through channel and has a second affinity to the sample of fluid medium, wherein the second affinity is greater than the first affinity. The different affinities enable the sample retaining means to collect a portion of a sample of fluid medium which flows through the flow-through channel and to retain the portion while a second fluid medium flows through and displaces the sample from the flow-through channel.

The method of loading also comprises causing the sample to flow through the flow-through channel and to be retained by the sample retaining means, and causing a displacing fluid to flow through the flow-through channel and displace the sample of fluid medium from the flow-through channel without displacing sample from the sample retaining means, wherein the sample retaining means has a greater affinity for the sample than for the displacing fluid. The displacing fluid thereby covers, entraps, encircles, and/or surrounds, and isolates the sample retained by the sample retaining means on at least one side of the retained sample.

According to some methods of loading, the displacing fluid is preferably substantially immiscible with the sample of fluid medium, and more preferably, is essentially or completely immiscible with the sample. According to embodiments of the invention, the sample comprises an aqueous medium. According to embodiments of the invention, the displacing fluid may comprise a curable fluid, preferably a curable adhesive.

According to some methods of loading, the flow-through channel has an entrance opening for introducing sample to the channel, and an exit vent for the escape of displaced air, sample or excess displacing fluid from the channel, and the method further comprises introducing the displacing fluid to the channel through the entrance opening and causing sample in the channel to be displaced by the displacing fluid. The displacing fluid may cause excess sample to exit the assembly through the exit vent, particularly in embodiments wherein the displacing fluid is forced into the assembly by other than capillary forces, for example, by pressure loading. In some embodiments, the exit vent may comprise a porous or absorbent material such as paper, or other materials that are wettable by the sample.

According to some embodiments, the method further comprises sealing the entrance opening and exit vent after the displacing fluid displaces sample from the channel. In some embodiments, the displacing fluid cures to seal the entrance opening and the exit vent. Preferably, the displacing fluid cures adjacent to the sample retaining means to seal the sample within the sample retaining means. In some embodiments, the sample retaining means retains about 1 microliter to about 1 picoliter of sample or less, preferably about 10 nanoliters of sample or less, and for some embodiments, about 1, nanoliter or less.

According to embodiments of the invention, methods are also provided for determining the existence and/or quantitation of multiple types of nucleic acid target molecules. According to some embodiments, different amplification targeting reagents can be loaded separately or together with respective different samples to be amplified. According to some embodiments, different amplification targeting reagents are preloaded into different sample retaining means within a single assembly, for example, an assembly having two parallel but separated flow-through channels having respective sample retaining means in communication with one of the channels. According to some embodiments, each sample retaining means contains a specific primer, pair of primers, and/or probe and at least one of the sample retaining means contains a primer or probe that differs from the primer or probe of a second retaining means. A sample possibly containing more than one different target sequence to be amplified is then introduced and retained by the sample retaining means. When isolated, amplified and quantitated, the existence and quantitation of two or more different target sequences can be determined, for example by using a fluorescence energy transfer assay. According to the invention, the device is permanently sealed with a curable adhesive and a homogeneous assay is performed. The sealed assay does not require physical separation of components of the assembly to determine whether specific target sequences have been amplified.

The invention will now be described with reference to the drawing figures which are exemplary in nature and not intended to limit the scope of the invention in any respect.

FIG. 1 shows an exploded view of an analytical assembly according to an embodiment of the present invention, shown in partial cutaway. The assembly comprises a substrate 20 and a cover 22. In the embodiment depicted, the substrate and cover comprise substantially rigid plates such as microscope slides, but may comprise more flexible materials such as microscope slide coverslips. The substrate includes a bottom plate 23 having an inner surface 24, and a patterned layer 26 of a first material disposed on the inner surface. The first material may be a patterned layer comprising a hydrophobic material, and provides the substrate 20 with a facing surface 28 which faces the cover 22. Within the patterned layer 26 of the first material are formed a plurality of wells or holes therethrough defining sample chambers 30. Each sample chamber 30 has a closed lower end 32, defined by the inner surface 24 of the bottom plate 23. Each sample chamber also has a sidewall which extends from the closed lower end 32 up to the facing surface 28 of the substrate. In some embodiments, the sample chamber extends up through the flow-through channel.

The cover 22 comprises a top plate 34 and a facing surface 36 which may comprise the same material as the top plate or a patterned layer 38 of a second material disposed on the inner surface of the top plate. The second material may be the same as the first material, and in some embodiments is preferably moderately hydrophobic, that is, it preferably has a surface energy of from about 30 dynes/cm to about 50 dynes/cm. Exemplary materials for the second material include silanes, methacrylates, epoxies, acrylates, cellulosics, urethanes, silicones, and materials having good adhesion to the displacing fluid, for example, materials having good adhesion to displacing fluids comprising curable adhesives. The patterned layer 38 may be smooth and of uniform thickness or it may have a plurality of sample chambers formed therein complementary to the chambers formed in patterned layer 26.

When assembled, the substrate 20 and cover 22 are attached together, with the facing surface 36 of the cover being spaced from the facing surface 28 of the substrate. The space between the facing surfaces 36 and 28 defines a flow-through channel through which sample fluid and displacing fluid may travel. The facing surfaces 36 and 28 are maintained spaced apart by spacer strips 40, which may comprise transfer adhesive strips, films or adhesive layers applied to edge regions of the substrate. In embodiments wherein a spacer strip is used and comprises an adhesive material, the spacer may also provide means to hold the substrate and cover together. Other means of holding the substrate and cover together may be used and include clips and clamps. According to some embodiments, hydrophobic spacer materials are preferred.

As can be seen in FIG. 1, the spacer strips are disposed along the longitudinal edges of facing surface 28 but are not included on the lateral edges of the facing surface 28. Thus, a gap is provided at the lateral edges of the assembled device and can be employed as an entrance opening and/or an exit vent.

When assembled, a sample of fluid medium, for example, an aqueous PCR sample, can be introduced to the flow-through channel by entering a gap at a lateral edge of the assembly. The sample flows through and fills the flow-through channel and the sample chambers, which are in fluid communication with the flow-through channel. Then, a displacing fluid is caused to enter the flow-through channel through a gap at a lateral edge of the assembly, and the displacing fluid flows through and fills the channel displacing sample from within the channel but without displacing sample from the sample chambers. The result is a plurality of discrete, isolated portions of the sample, held by the sample chambers.

According to the embodiment of FIG. 1 and other embodiments, sample chambers having dimensions of a few microns in diameter and a few microns in depth can be provided, and result in sample chamber volumes of about 10 picoliters or less. In embodiments wherein sample chambers are provided having diameters of about 0.5 millimeter and depths of about 0.05 millimeter, sample volumes of about 10 nanoliters can be achieved.

The flow-through channel may have a depth of about 0.1 to about 500 microns, preferably from about 10 to about 100 microns.

FIG. 2 is an exploded view of an analytical assembly according to an embodiment of the present invention, shown in partial cutaway. The assembly comprises a substrate 50 and a cover 52. In the embodiment depicted, the substrate and cover comprise substantially rigid plates such as microscope slides, but may comprise more flexible materials such as microscope slide coverslips. The substrate includes a bottom plate 53 having an inner surface 54, and a patterned layer 56 of a first material disposed on the inner surface. The first material may be a patterned layer comprising a hydrophobic material, and provides the substrate 50 with a facing surface 58 which faces the cover 52. Within the patterned layer 56 of the first material are formed a plurality of wells or holes therethrough defining bottom portions 60 of sample chambers. Each sample chamber bottom portion 60 has a closed lower end 62, defined by the inner surface 54 of the bottom plate 53. Each sample chamber also has a sidewall which extends from the closed lower end 62 up to the facing surface 58 of the substrate.

The cover 52 comprises a top plate 64 and a facing surface 66 which comprises a patterned layer 68 of a second material. The second material may be the same as the first: material, and in some embodiments is preferably moderately hydrophobic, that is, it preferably has a surface energy of from about 30 dynes/cm to about 50 dynes/cm. The patterned layer 68 may be smooth and of uniform thickness or, as shown in FIG. 2, the patterned layer 68 may have a plurality of upper portions 69 of sample chambers formed therein which are complementary to the bottom portions 60 formed in patterned layer 56.

When assembled, the substrate 50 and cover 52 are attached together, with the facing surface 66 of the cover being spaced from the facing surface 58 of the substrate. The space between the facing surfaces 66 and 58 defines one or more flow-through channels through which sample fluid and displacing fluid may travel. Entrance openings 70 in the form of holes through the cover 52 are provided for the sample fluid and displacing fluid to enter the flow-through channel. Two entrance openings 70 are provided as the assembly depicted in FIG. 2 comprises two flow-through channels. An exit vent (not shown) is provided for each flow-through channel and may comprise a hole formed through the substrate or cover and in communication with the flow-through channel. The facing surfaces 66 and 58 are maintained spaced apart by spacer strips 72, which may comprise transfer adhesive strips or patterned layer applied to edge regions of the substrate. In embodiments wherein a spacer strip is used and comprises an adhesive material, the spacer may also provide means to hold the substrate and cover together. Other means of holding the substrate and cover together may be used and include clips and clamps. According to some embodiments, hydrophobic spacer materials are preferred.

According to some embodiments of the invention, for example, some embodiments similar to that of FIG. 2, a centrally located entrance opening in the top plate can be provided and a sample fluid and/or displacing fluid can be loaded into the assembly by capillary force, centrifugal force, or other loading techniques.

As can be seen in FIG. 2, the spacer strips 72 are disposed along the entire peripheral edge of facing surface 58. A spacer strip 74 may also be included to divide the assembly into different portions. As shown in FIG. 2, spacer strip 74 divides the assembly into first and second halves, 76 and 78, respectively.

When assembled, the lower and upper portions of the sample chambers complement one another to form a plurality a sample chambers, each having a closed lower end, a closed upper end, and a communication to a flow-through channel, the communication of each chamber being formed in the sidewall of the chamber. A sample of fluid medium, for example, an aqueous PCR sample, can be introduced to the flow-through channels through entrance openings 70. The sample flows through and fills the flow-through channels and both the lower and upper portions of the sample chambers, which, are in fluid communication with the respective flow-through channels. Then, a displacing fluid is caused to enter the flow-through channels through the entrance openings 70, and the displacing fluid flows through and fills the channels displacing sample from within the channels but without displacing sample from the sample chambers. The result is a plurality of discrete, isolated portions of the sample, held by the sample chambers. According to some embodiments of the invention, two different sample fluids are used, one in each half (76, 78) of the assembly.

FIG. 3 is a cross-sectional view through a longitudinal central portion of an analytical assembly according to another embodiment of the present invention. The assembly of FIG. 3 comprises a substrate 90 and a cover 92. In the embodiment depicted, the substrate and cover comprise substantially rigid plates such as microscope slides, but may comprise more flexible materials such as films or microscope slide coverslips. The substrate includes a bottom plate 93 having an inner surface 94, and a patterned layer 96 of a first material disposed on the inner surface. The first material may be a patterned layer comprising a hydrophobic material, and provides the substrate 90 with a facing surface 98 which faces the cover 92. Within the patterned layer 96 of the first material are formed a plurality of wells or holes therethrough defining bottom portions 100 of sample chambers. Each sample chamber bottom portion 100 has a closed lower end 102, defined by the inner surface 94 of the bottom plate 93. Each sample chamber also has a sidewall which extends from the closed lower end 102 up to the facing surface 98 of the substrate.

The cover 92 comprises a top plate 104 and a facing surface 106 which comprises a patterned layer 108 of a second material. The second material may be the same as the first material, and in some embodiments is preferably moderately hydrophobic, that is, it preferably has a surface energy of from about 20 dynes/cm to about 30 dynes/cm. The patterned layer 108 may be smooth and of uniform thickness or, as shown in FIG. 3, the patterned layer 108 may have a plurality of upper portions 109 of sample chambers formed therein which are complementary to the bottom portions 100 formed in patterned layer 96.

The substrate 90 and cover 92 are attached together, with the facing surface 106 of the cover being spaced from the facing surface 98 of the substrate. The space between the facing surfaces 106 and 98 defines one or more flow-through channels 110 through which sample fluid and displacing fluid may travel. An entrance opening 112 in communication with the flow-through channel 110, in the form of a gap formed at a lateral end of the assembly, is provided for the sample fluid and displacing fluid to enter the flow-through channel 110. An exit vent 114 is provided for sample to exit the channel 110 as the sample is displaced from the channel by the displacing fluid. The entrance opening and exit vent may instead be in the form of holes formed through the substrate and/or cover. The facing surfaces 106 and 98 are maintained spaced apart by spacer strips 116, which may comprise transfer adhesive strips or a patterned layer applied to edge regions of the substrate. In embodiments wherein a spacer strip is used and comprises an adhesive material, the spacer may also provide means to hold the substrate and cover together. Other means of holding the substrate and cover together may be used and include clips and clamps.

As can be seen in FIG. 3, the spacer strips are disposed along the longitudinal edges between the facing surfaces but are not included on the lateral edges of the of facing surfaces. Thus, gaps used as the entrance opening and exit vent are provided at the lateral edges of the device.

As can be seen in FIG. 3, the lower portions 100 and upper portions 109 of the sample chambers complement, one another to form a plurality a sample chambers 118, each having a closed lower end, a closed upper end, and a communication to a flow-through channel, the communication of each chamber being formed in the sidewall of the chamber. A sample of fluid medium, for example, an aqueous PCR sample, can be introduced to the flow-through channel 110 through entrance openings 112. The sample flows through and fills the flow-through channel and both the lower and upper portions of the sample chambers. Then, a displacing fluid is caused to enter the flow-through channel through the entrance openings, and the displacing fluid flows through and fills the channel displacing sample from within the channel but not displacing sample from the sample chambers. The result is a plurality of discrete, isolated portions of the sample, held or retained by the sample chambers. The sample fluid retained in the sample chambers may form a cylinder extending from the closed lower, through and interrupting the flow-through channel, and up to the closed upper end.

Figure 4:
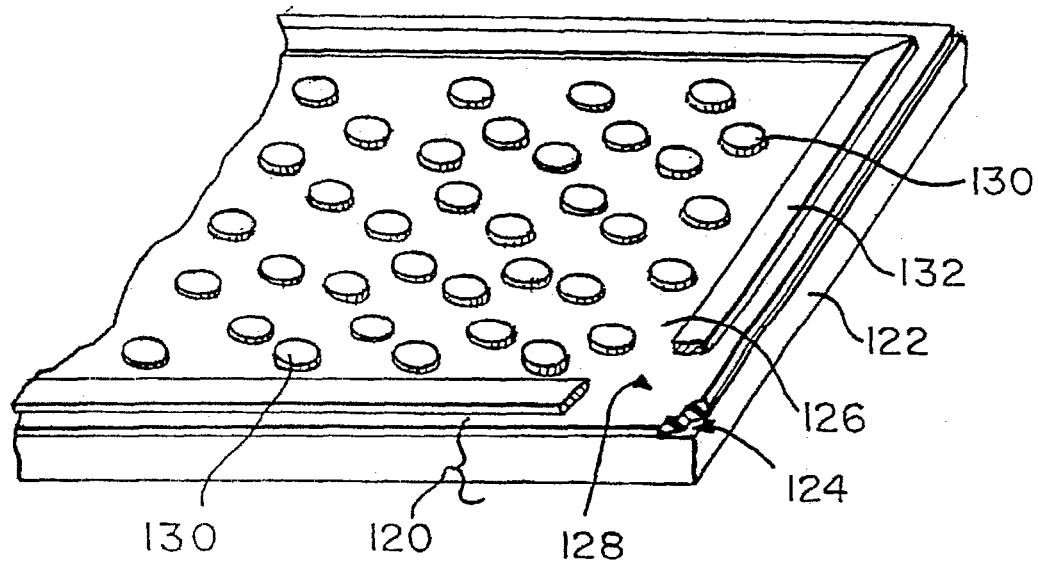
FIG. 4 is a perspective view of a bottom portion of an analytical assembly according to an embodiment of the present invention, the bottom portion comprising sample retaining means in the form of patches of fluid retaining material formed on a patterned layer coated on the inner surface of a bottom plate.

FIG. 4 is a perspective view of a bottom portion of an analytical assembly according to an embodiment of the present invention, with the cover removed. The bottom portion of the assembly comprises a substrate 120, depicted in the figure as a coated substantially rigid plate such as microscope slide. The substrate includes a bottom plate 122 having an inner surface 124, and a patterned layer 126 of a first material disposed on the inner surface. The patterned layer has a substantially uniform thickness. The first material may comprise a hydrophobic material, and provides the substrate 120 with a facing surface 128 which faces a cover (not shown), for example, the cover used in the embodiment of FIG. 1. On the patterned layer 126 are formed a plurality of patches 130 of sample retaining material, preferably capable of retaining a fluid sample volume of from about 1 microliter to about 1 picoliter or less. Adhesive strips, a patterned layer of pressure sensitive adhesive, or a patterned layer of a curable adhesive, 132, may be used to attach a cover to the bottom portion.

According to some embodiments, the patch occupies a volume of about 100 nanoliters or less. The patch may be an absorbent material which absorbs and retains sample, or the patch may be made of material which has an affinity sufficient enough to retain, for example, an aqueous PCR sample. According to some embodiments, the patches of material comprise a hydrophilic material. According to embodiments of the invention wherein the sample retaining patches comprise a substantially non-absorbent material which has a retaining affinity for a sample, the patch defines a closed lower end of a sample chamber defined between the exposed surface of the patch and the facing surface of a cover. In some embodiments, a patch of porous material may fill a volume between the substrate and the cover and the sample chamber is defined by the void volume of the porous patch.

Figure 5:
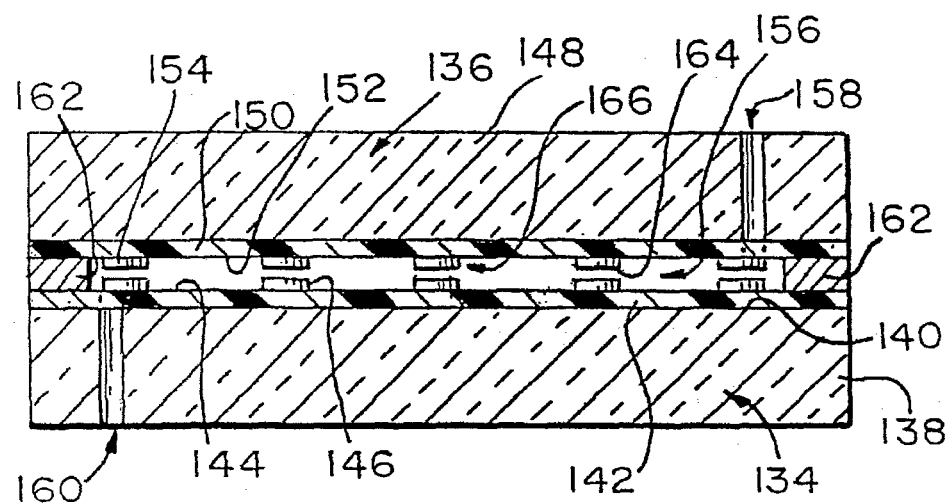
FIG. 5 is a cross-sectional view through a longitudinal central portion of an analytical assembly according an embodiment of the present invention.

FIG. 5 is a cross-sectional view through a longitudinal central portion of an analytical assembly according an embodiment of the present invention wherein sample chambers comprise absorbent material patches or comprise the volume between complementary opposing patches of sample retaining materials.

The assembly of FIG. 5 comprises a substrate 134 and a cover 136 attached to one another. In the embodiment depicted, the substrate and cover comprise substantially rigid plates such as microscope slides. The substrate includes a bottom plate 138 having an inner surface 140, and a patterned layer 142 of a first material disposed on the inner surface. The first material may be a hydrophobic material, and provides the substrate 134 with a facing surface 144 which faces the cover 136. On the patterned layer 142 are formed a plurality of sample retaining patches 146 which define sample chambers by absorbency or surface energy or other retentive property.

The cover 136 comprises a top plate 148 and a patterned layer 150 of a second material defining a facing surface 152. The second material may be the same as the first material, and in some embodiments is preferably a hydrophilic material if aqueous samples are to be retained and isolated. The patterned layer 150 may be smooth and of uniform thickness or, as shown in FIG. 5, the patterned layer 150 may have a plurality of sample retaining patches 154 complementary to and mirroring patches 146.

The substrate 134 and cover 136 are attached together, with the facing surface 152 of the cover being spaced from the facing surface 144 of the substrate. The space between the facing surfaces 152 and 144 defines one or more flow-through channels 156 through which sample fluid and displacing fluid may travel. An entrance opening 158 comprising a hole formed through the cover and in communication with the flow-through channel 156. An exit vent 160 comprising a hole through the substrate 134 is provided for sample to exit the channel 156 as the sample is displaced from the channel by the displacing fluid.

The facing surfaces 152 and 144 are maintained spaced apart by spacer strips 162, which may comprise transfer adhesive strips applied to edge regions of the substrate. In embodiments wherein a spacer strip is used and comprises an adhesive material, the spacer may also provide means to hold the substrate and cover together. Other means of holding the substrate and cover together may be used and include clips and clamps.

According to some embodiments, the patches comprise an absorbent sample retaining material. According to some embodiments, the patches retain sample by surface energy, and have an affinity for a sample, for example, a hydrophilic material patch which retains an aqueous sample on a surface 164 thereof. In some embodiments, the affinity may be induced by optical or electromagnetic means. The sample chamber may comprise the volume 166 between the facing surfaces of each complementary pair of patches, wherein the sample chambers have no sidewalls but are defined as the volume between the two complementary patch surfaces. The affinity of the two opposing patch surfaces to a retained sample is sufficient to support a column of sample between the two patches while a displacing flows through the channel adjacent the column. In some embodiments, patches of porous material extending from the substrate to the cover may interrupt the flow-through channel and the sample chamber may be defined as the void volume of a porous patch.

Sample flows through and fills the flow-through channel and the sample chambers, which are in fluid communication with the flow-through channel. A displacing fluid can subsequently be caused to enter the flow-through channel through the entrance opening, displacing sample from within the channel but not displacing sample from the sample chambers. The result is a plurality of discrete, isolated portions of the sample, held or retained or absorbed by the sample chambers.

Figure 6A:
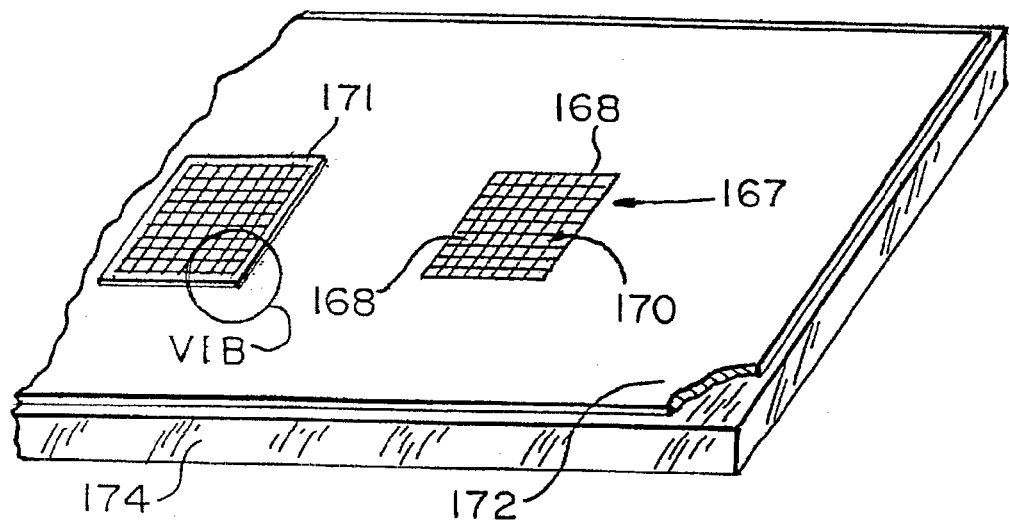
FIG. 6A is a perspective view of a bottom portion of an analytical assembly according to another embodiment of the present invention.
Figure 6B:
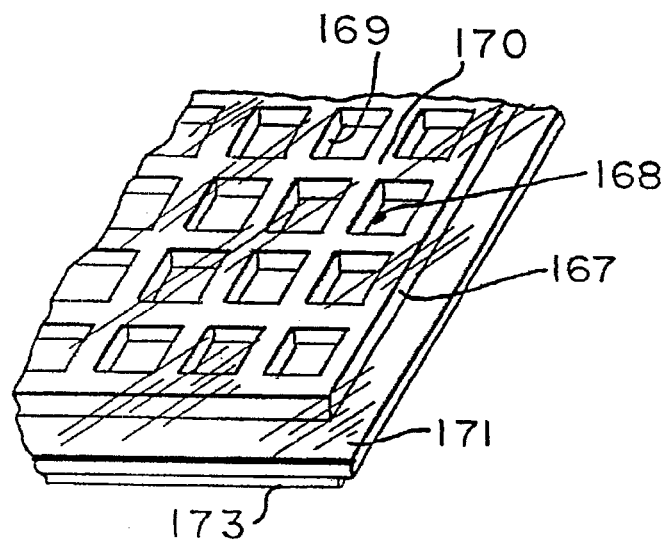
FIG. 6B is an enlarged view of portion VIA shown in FIG. 6A.

FIG. 6A is a perspective view of another embodiment of the present invention, and FIG. 6B shows an enlargement of portion VIB from FIG. 6A. As can be seen in FIGS. 6A and 6B, a bottom support plate 174 supports a sample retaining means 167 comprising a plurality of pores or cavities 168 having open ends in communication with an exposed surface 170 on which a sample of fluid is applied. The pores have a first affinity to a sample of fluid medium such that when the sample is disposed upon the exposed porous surface 170 the sample is drawn into and retained by the plurality of pores 168. For example, through capillary or other force, the sample may wet and fill the pores 168. The pores 168 have substantially the same volume as one another and each has a closed lower end 169. Preferably the pores 168 each have a volume of about 1 µl or less, more preferably, about 10 nl or less, and for some applications about 1 nl or less. The closed lower ends 169 of the pores are defined or bound by a layer of coating material 172 deposited on a bottom plate 174. The coating material may be a hydrophilic material if aqueous samples are to be retained in the pores.

A cover 171 is provided on one of the sample retaining means shown in FIG. 6A. The cover 171 can be used to displace sample fluid from the porous surface 170 of the retaining means and for sealing sample within the pores 168. The cover 171 displaces sample fluid from the porous surface without displacing sample from within the pores. Preferably, the cover 171 comprises a hydrophobic coating 173 on the surface of the cover which contacts the exposed surface 170 of the sample retaining means. The coating 173 contacts sample and can be used to squeeze excess sample off of the surface 170. A means for sealing the sample of fluid within the pores is also provided, and in the embodiment shown in FIG. 6B the means for displacing excess sample and the means for sealing sample in the pores are the same means, that is, the cover 171. Preferably, the coating 173 is adhesive as well as hydrophobic, although an adhesive and/or hydrophobic coating may instead or additionally be provided in the exposed surface 170 of the sample retaining means. Sealing the sample in the pores prevents evaporation and contamination of the sealed sample.

The displacing means and the sealing means, for example the cover 170 shown in FIGS. 6A and 6B, may be pressed against the exposed surface 170 by any of a variety of means. Clamps, clips or springs may be used to attach the sealing means to the exposed surface 170, and/or to force the displacing means against the exposed surface.

According to some embodiments of the invention, other means may be used as displacing means for a device similar to, or the same as, that shown in FIGS. 6A and 6B. For example, according to some embodiments, a drop or bead of curable fluid, for example, a curable adhesive, can be forced across an exposed surface of a sample retaining means having one or more sample retaining cavity, recess, hole or pore formed in the surface. Gravity, pressurized gas, or mechanical means, for example, can be used to force the curable fluid across the exposed surface, displacing excess sample from the surface without displacing sample from within the sample retaining cavity. According to some embodiments of the invention, as the curable fluid traverses the exposed surface a thin layer of the fluid is deposited on the surface and coats the top of a sample portion retained in the cavity. Upon curing, the curable fluid forms a seal, for the sample retained within the cavity such that the sample retained is isolated from other cavities and from excess sample. The sealed sample is protected from contamination and evaporation. Preferably, the curable fluid seal, is sufficient to prevent contamination and evaporation of the entrapped sample during thermal cycling conditions generally used in PCR amplification methods.

According to some embodiments of the invention, separate displacing means and sealing means are provided for isolating a sample portion within a sample retaining cavity. For example, according to embodiments of the invention, a displacing means is provided for removing excess sample from an exposed surface of a device having a sample retaining cavity associated therewith. The sample retaining cavity may be formed on, formed in, in contact with or adjacent to a substrate. The cavity may be defined by at least one sidewall, and the sidewall may comprise a hydrophilic material. The displacing means may comprise a wiping device such as a squeegee, a wiper, a blade or other scraping or rubbing device which can physically move excess sample away from the open upper end of a sample retaining cavity and preferably off of the exposed surface of the sample retaining means. Preferred displacing means may comprise a wiping device made of an elastomeric material, for example, a stiff silicone rubber blade. Preferably, the wiping device comprises a hydrophobic material to which aqueous sample fluids will not cling.

According to some embodiments, the displacing means comprises an opening or channel through which a sample retaining means snugly fits, and a wiping device is provided adjacent to the opening or channel such that the wiping device wipes excess sample from an exposed surface of the sample retaining means as the retaining means is forced through the opening or channel.

According to some embodiments of the invention, sealing means are applied to the sample retaining cavity immediately after the displacing means displaces excess sample from adjacent the sample retaining cavity. When retained sample portions having volumes of about 1 µl or less are formed, they tend to evaporate rapidly and thus require prompt sealing to protect sample integrity. According to some embodiments of the invention, a wiping device is used to displace excess sample fluid from an exposed surface of a sample retaining means, and the wiping device is provided with a trailing edge that pulls a bead or drop of a curable sealing fluid across the exposed surface as a leading edge of the wiping device displaces excess sample.

Example 1 and Control 1

Conventional PCR was performed in 0.2 ml polypropylene ependorf tubes to set standards. Microcapillary PCR was then performed according to the present invention on the same sample material in quartz glass microcapillaries. The PCR sample containing the nucleic acid sequence to be amplified was prepared and included materials from a "TaqMan" kit available from Perkin-Elmer, Applied Biosystems Division, Foster City, Calif. The kit contained human DNA at 10 ng/µl, the forward primer 5'-TCACCCACACTGTGCCCATC-TACGA-3' (SEQUENCE ID NO:1) and the reverse primer 5'-CAGCGGAACCGCTCATTGCCAATGG-3' (SEQUENCE ID NO:2) that amplify a 295 bp segment of the human β actin gene, and a dual fluor-labeled probe comprising 5'-[6FAM]-ATGCCC-[TAMRA]-CCCCCATGCCATC-CTGCGT-3' (SEQUENCE ID NO:3) that is complementary to bases 31 to 56 of the PCR product. The designation FAM represents 6-carboxyfluorescein, and TAMRA represents 6-carboxytetramethyl-rhodamine. With reference to the Control 1 and Example 1, the term "FAM" is referred to herein as "fluorescein" and the term "TAMRA" is referred to herein as "rhodamine".

The PCR sample comprised Tag polymerase available from Boehringer Mannheim, Indianapolis, Ind., and anti-Taq antibody from Clonetech, Palo Alto, Calif. The sample also comprised concentrations of 10 mM Tris-HCl (pH 8.3), 50 mM KCl, about 0.01% by weight gelatin, 500 µg/ml to 5 mg/ml bovine serum albumin (BSA), 3.5 mM $MgCl_2$, 0.2 mM each of DATP, dCTP, dGTP and dUTP, 0.3 µM forward and reverse primers, 0.2 µM dual-fluor-labeled probe, 0.5 manufacturer's units (u) Taq polymerase per 10 µl, PCR mixture, 0.1 µl anti-Taq antibody per 10 µl PCR mixture, and varying amounts of template DNA. The specific activity of Tag polymerase was about 250,000 units per mg which, at a molecular weight of 100,000 Daltons, translates to about $10^9$ molecules per µl. Since β actin is a single copy gene, it was estimated that there is one copy of β actin template per 3 pg of human genomic DNA. In some PCRs the dual-fluor-labeled probe was replaced with the fluorescent, DNA-staining dye SYBR™ Green I (product # S-7567) available from Molecular Probes, Eugene, Oreg., used a $10^{-4}$ dilution from the stock supplied by the manufacturer.

The conventional PCRs (CONTROL 1) performed in the 0.2 ml polypropylene tubes were thermocycled in a model 9600 thermocycler from Perkin Elmer using 92° C. for 15 seconds, 54° C. for 15 seconds, and 72° C. for 15 seconds, for 40 cycles.

Microcapillary PCR was performed according to the present invention in quartz glass microcapillaries from Polymicro Technologies (Phoenix, Ariz.). These capillaries had inner diameters ranging from 20 µm to 75 µm and outer diameters of 250 µm to 375 µm. The capillaries come with either a polyimide or Teflon external coating to make them flexible. Because the polyimide coating is opaque and fluorescent, it had to be removed before use. The coating was removed by flaming a segment of polyimide capillary with a Bunson burner for several seconds and then gently wiping off the burned coating. Flaming and wiping was repeated as necessary until the capillary was clear. The resulting bare capillaries were very fragile. The Teflon coated microcapillaries were easier to work with since the optically clear and non-fluorescent Teflon coating did not need to be removed. Both types of capillaries gave equivalent results in PCR.

Hundreds of microcapillary tubes (EXAMPLE 1) were filled by touching an open end to a drop of the PCR sample which wicked in by capillary action. The microcapillaries were then sealed and supported by gluing the two ends thereof to two respective coverslips, leaving an unsupported segment in the middle, thus minimizing thermal mass. A I-curable fluid glue was used to seal the end of the tube and to glue the tube ends to coverslips. Assemblies comprising a plurality of microcapillaries were formed by sealing the ends of each tube in the assembly to the same pair of coverslips.

The glue was available as optical adhesive #81 from Norland Products, New Brunswick, N.J. The glue was cured by exposure to 366 nm UV light. A source of 366 nm wavelength light is UV lamp model UVL-21, available from UVP Inc., San Gabriel, Calif. The lamp was held about 1 cm from the sample for 30 seconds. The PCR mixture was shielded from UV light by laying a small piece of opaque paper over the center section of the capillary during UV exposure.

FIG. 7 is a top plan view of an exemplary microcapillary device used in accordance with Example 1, of the present invention. As shown in FIG. 7, an assembly 176 is provided having four microcapillary tubes 178 having inner diameters of about 100 microns each, and two support tubes 180 having outer diameters of about 1.5 mm. The ends of the tubes 178 and 180 were adhered to two respective plates or bases 182 with UV-curable adhesive 184. One end of each tube microcapillary and support tube shared a respective plate 182. In the embodiment shown in FIG. 7, the plates comprised standard 1"×1" microscope cover slips and the tubes were each about 4 cm long. All the tubes were arranged substantially parallel to one another with the microcapillary tubes 178 each being positioned between the two larger diameter support tubes.

The sample holding assembly 176 was attached with SCOTCH tape to the sample holder of a Rapidcycler air oven available from Idaho Technologies, Idaho Falls, Id., and cycled through a protocol comprising cycles of 92° C. for 5 seconds, 54° C. for 5 seconds, and 72° C. for 15 seconds, for 40 cycles. The cycling protocol took about 30 minutes in the Rapidcycler.

After PCR cycling, fluorescence of the samples was measured with a Zeiss Axiovert 410 laser scanning microscope using a 20X–0.5 NA objective, 15 mW external argon laser approximately 5% of the power of which was focused to a spot size of 1 $\mu m^2$, and band pass filters of 515-565 nm for fluorescein and SYBR™ Green, and >590 nm for rhodamine (power loss and spot size estimates provided from the manufacturer). Average pixel intensity was measured in regions of about 20 $\mu m \times 50 \mu m$ overlying the capillary image. Fluorescence intensity was examined visually along the 2.5 cm lengths of capillaries by manually translating the stage; quantitative measurements were made every 2-5 mm or more often if variability in the fluorescence signal was observed.

Results

When PCRs were performed in 20 µl volumes in ependorf tubes in a model 9600 Thermocycler (Perkin Elmer, Norwalk, Conn.), the B actin primers amplified an approximately 300 bp segment from human DNA as expected. PCRs performed in the presence of the TaqMan probe were transferred to capillary tubes and analyzed by fluorescence microscopy. Typical values for average pixel intensity were about 130 (relative fluorescence units) for fluorescein and about 60 for rhodamine, with values of background emission from empty capillaries of about 20 at both wavelengths. In different experiments the fluorescein:rhodamine (F/R) intensity ratio varied from about 1.0:1.0 to about 2.0:1.0 in samples containing PCR product. For negative control PCRs containing no template DNA, no Taq polymerase, or no reverse primer, the rhodamine emission was about the same (about 60), while the fluorescein emission was reduced to about 30, giving a F/R intensity ratio of about 0.5. The absolute values of fluorescein and rhodamine emission varied between experiments and with small changes in machine settings (laser power, attenuation, brightness, contrast) whereas the F/R intensity ratio was fairly constant. Therefore, the F/R intensity ratio was used as a measure of whether the β actin product had been amplified.

The yield of PCR product in conventional reactions in polypropylene tubes was estimated by ethidium bromide staining of product in agarose gels, and by adding a known amount of $^{32}P$-dCTP to a PCR and counting radioactivity in the purified PCR product. Both methods gave an estimate of about $10^{11}$ product molecules/µl of PCR. This corresponds to a product concentration of about 0.16 µM, which implies that about half of the PCR primers were converted to product.

To assess the extent of degradation of TaqMan probe following PCR, the effect of mung bean nuclease on the F/R intensity ratio was examined. Treatment of probe with mung bean nuclease for 10 minutes at 37° C. raised the F/R intensity ratio from 0.5 to 5. This presumably represents complete degradation since further incubation did not increase the ratio. An F/R intensity ratio of 1.5, characteristic of positive PCRs, therefore suggests that about 30% of probe was degraded. This corresponds to a concentration of degraded probe of 0.06 µM and implies that about one third of the probe that could have hybridized to PCR product was degraded.

When PCRs were performed in small diameter glass capillaries, the volume of the reaction was too small to detect PCR product by standard gel electrophoresis. While products might have been detectable by capillary electrophoresis, it was of interest to see whether the TaqMan assay could be used as a detection method. The F/R intensity ratio was therefore used as a surrogate measure of amplification. This ratio was about 0.5 in negative control reactions (no template, no enzyme, or no reverse primer) and was usually greater than 1 in samples where product was expected. In capillaries containing terminal dilutions of genomic DNA template, the ratio sometimes varied with position along the capillary, which was attributed to localized accumulation of degraded probe, discussed in more detail below. In cases where the intensity ratio varied, the maximum value of the F/R intensity ratio in the capillary was used as the measure of whether the target sequence had been amplified.

Figure 8:
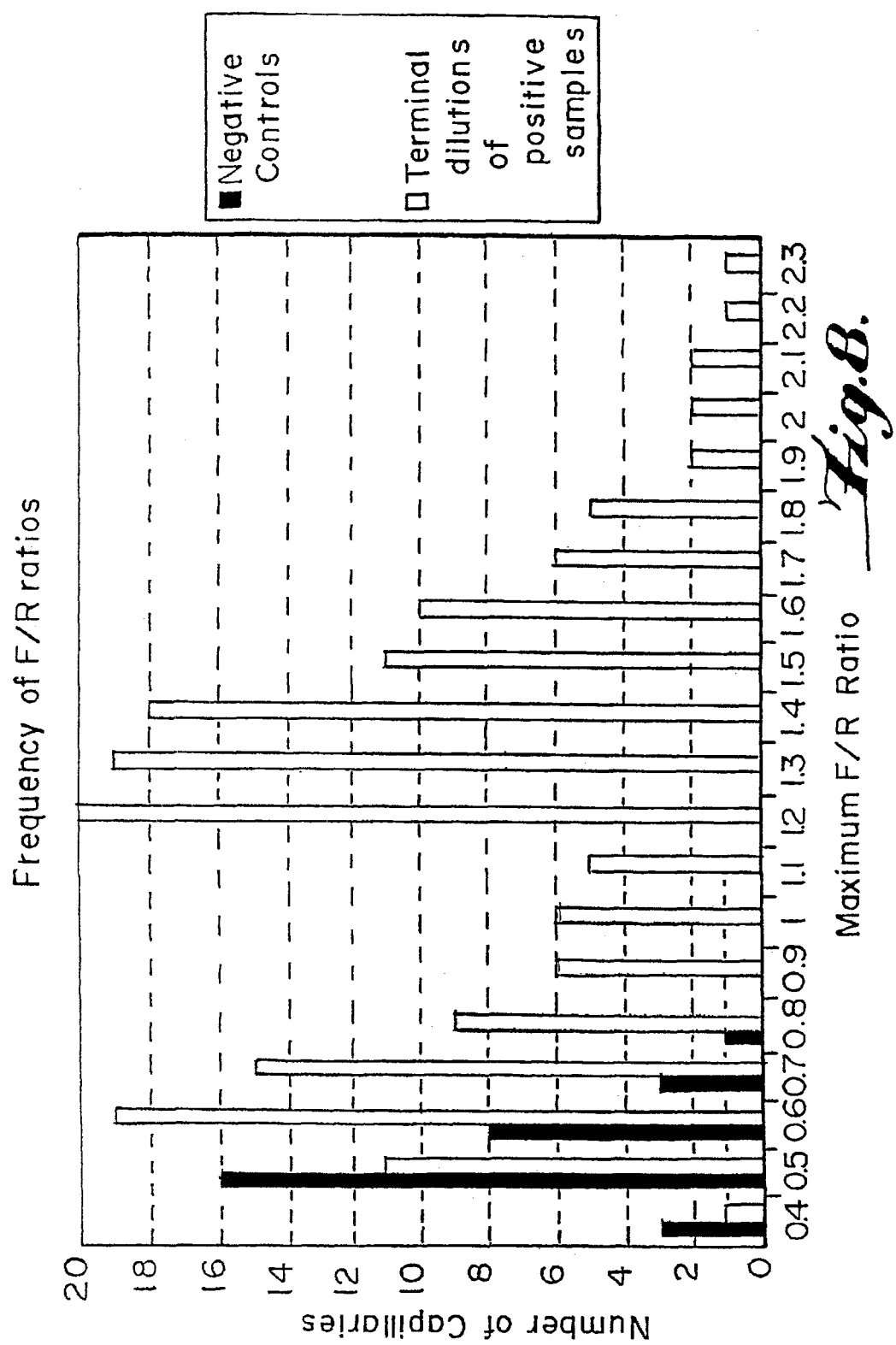
FIG. 8 is a histogram showing the maximum values of the fluorescein:rhodamine intensity ratio in over 100 capillary reactions of terminally diluted genomic DNA carried out in an assembly according to the present invention and according to a method according to the invention.
Figure 9:
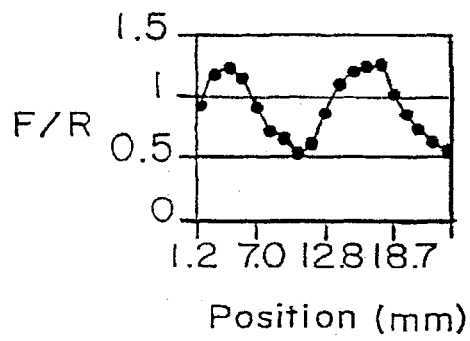
FIGS. 9-14 are plots of the fluorescein:rhodamine ratio along a few representative microcapillaries containing samples subject to PCR in accordance with the present invention.
Figure 10:
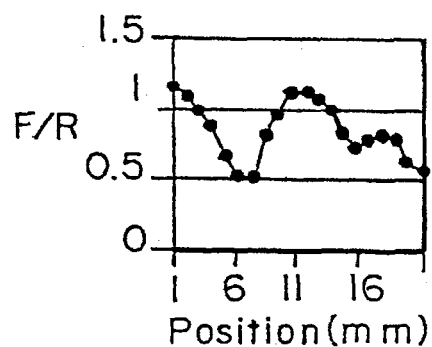
Figure 11:
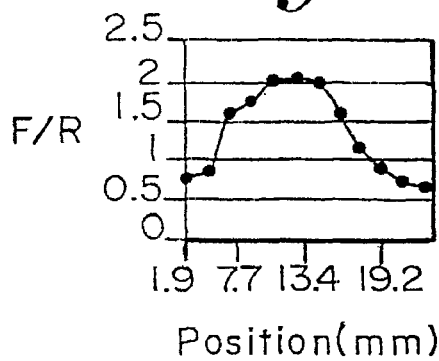
Figure 12:
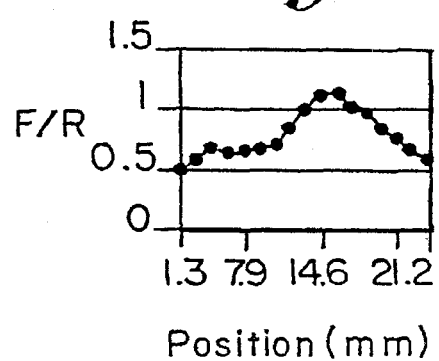
Figure 13:
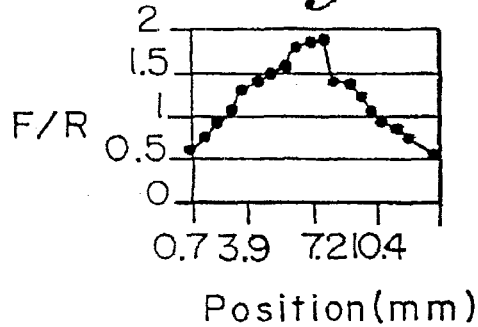
Figure 14:
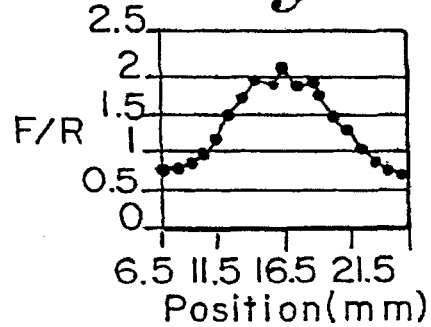

A histogram of the maximum values of the F/R intensity ratio in over 100 capillary reactions of terminally diluted genomic DNA is shown in FIG. 8, along with the corresponding values for negative control reactions. The negative controls had a mean ratio of 0.5 with a range of 0.4 to 0.9. The experimental samples had a bimodal distribution with one arm of the distribution paralleling that of the negative control samples. This suggests that the experimental samples consisted of positive and negative samples. Since the nadir of the experimental sample distribution occurred at about an F/R intensity ratio of 1, we chose this value as a "cut-off" to distinguish positive from negative samples. This "cut-off" is consistent with the F/R values of 1 to 2 in PCRs carried out in conventional volumes in ependorf tubes.

Using a "cut-off" of F/R≥1, the sensitivity of the detection system was estimated by mixing exonuclease-digested probe with undegraded probe. An F/R ratio of ≥1 was obtained when ≥0.02 µM degraded probe was mixed with 0.2 µM undegraded probe. This corresponds to about $10^8$ molecules of degraded probe in a 10 nl volume. Using the confocal feature of the microscope, it was determined that the signal decreased rapidly when the depth of field dropped below 20 µm. Thus, an estimate of the lower limit of detection for this system is about $10^5$ molecules of degraded probe in a volume of 20 µm×20 µm×20 µm, that is, about 10 picoliters (pl).

As has been noted by others performing PCR in glass tubes, for example in the publication of Wittwer et al., *Rapid Cycle DNA Amplification: Time and Temperature Optimization*, BioTechniques, Vol. 10, pp. 76-83 (1991), it was important to include bovine serum albumin (BSA) in the PCRs. Presumably, BSA blocks non-specific sticking of DNA to glass. When BSA was not included, the F/R intensity ratio was about 0.5. Generally, a 500 µg/ml final concentration of BSA was used in the PCRs although for some batches of BSA the concentration was increased to 5 mg/ml.

Human DNA was diluted so that PCRs contained 0-14 haploid genome equivalents (0-42 pg)/capillary. Reactions were scored as positive if the maximum F/R intensity ratio along the tube was 1.0 or greater. The results for a series of PCRs in capillaries with internal diameters of 20 to 75µ are shown in Table 1 below and shown graphically in FIG. 8.

TABLE 1

Replicate PCRs in microcapillaries with terminal dilutions of genomic DNA

| Capillary diameter (microns) | Haploid genome equivalents per capillary, m | Probability of ≥1 template per capillary $1-e^{-m}$ | Fraction positive PCRs | Number of PCRs |
|---|---|---|---|---|
| 20 | 0 | 0.00 | 0.00 | 2 |
|  | 0.2 | 0.18 | 0.10 | 10 |
|  | 0.5 | 0.39 | 0.33 | 15 |
| 25 | 0 | 0.00 | 0.00 | 4 |
|  | 0.4 | 0.33 | 0.28 | 18 |
|  | 0.8 | 0.55 | 0.50 | 8 |
|  | 1.5 | 0.78 | 1.00 | 3 |
|  | 3 | 0.95 | 1.00 | 3 |
| 30 | 0 | 0.00 | 0.00 | 8 |
|  | 0.5 | 0.39 | 0.52 | 23 |
|  | 1 | 0.63 | 0.92 | 13 |
|  | 1.5 | 0.78 | 1.00 | 10 |
|  | 4 | 0.98 | 1.00 | 3 |
| 50 | 0 | 0.00 | 0.00 | 13 |
|  | 0.4 | 0.33 | 0.00 | 3 |
|  | 0.8 | 0.55 | 0.67 | 27 |
|  | 1.5 | 0.78 | 0.82 | 28 |
|  | 3 | 0.95 | 1.00 | 2 |
|  | 6 | 1.00 | 0.89 | 9 |
|  | 13 | 1.00 | 1.00 | 7 |
| 75 | 0 | 0.00 | 0.00 | 7 |
|  | 0.8 | 0.55 | 0.50 | 6 |
|  | 1.7 | 0.82 | 0.67 | 12 |
|  | 3.4 | 0.97 | 1.00 | 9 |
|  | 7 | 1.00 | 1.00 | 5 |
|  | 14 | 1.00 | 1.00 | 6 |

Capillaries containing more than one haploid genome equivalent generally had F/R intensity ratios greater than 1. In capillaries containing less than one haploid genome equivalent, the fraction of capillaries with F/R intensity ratio ≥1 was roughly proportional to the fraction of capillaries expected to contain 1 or more template molecules. This fraction was calculated from the Poisson distribution as $1-e^{-m}$ where m=the amount of DNA/capillary/3 pg. The results provide strong support for the hypothesis that reactions were positive when capillaries contained 1 or more template molecules.

Example 2

Similar results were obtained with another preparation of human genomic DNA obtained from Promega: at 8 haploid genome equivalents (24 pg) per capillary, 4 of 4 capillaries gave maximum F/R intensity ratios ≥1; at 0.7 haploid genome equivalents (2 pg) per capillary, 3 of 4 capillaries were positive; at 0.1 haploid genome equivalents (0.4 pg) per capillary, 0 of 4 capillaries were positive.

Example 3

The inhomogeneity of F/R intensity ratio along the length of capillaries containing about 1 template molecule suggested that residual localization of degraded probe may be observed as a result of localized accumulation of PCR product. To investigate this possibility, amplifications in 2.5 cm long sections of capillaries containing about 0.5 haploid genome equivalent per capillary were performed. A plot of F/R intensity ratio along a few representative capillaries is shown in FIGS. 9-14. Some capillaries had a single peak while others had two. Two peaks indicate two areas where PCR product and degraded probe had accumulated. The half-widths of the peaks (measured at half-height) were about 3-6 mm. When capillaries were left overnight, the distributions broadened and flattened. Inhlomogeneities in F/R intensity ratio were not seen when capillaries were examined before PCR, or after PCR in capillaries containing no template DNA or about 75 initial template molecules. Representative experiments are shown in Table 2 below. The results indicate that high variability in the F/R intensity ratio is specific for capillaries with about 1 target molecule and decreases with time.

TABLE 2

| GROUP | HAPLOID GENE EQUIVALENTS PER CAPILLARY | TIME WHEN FLUORESCENCE ANALYZED | NUMBER OF CAPILLARIES | NUMBER OF CAPILLARIES WITH MAXIMUM F/R INTENSITY RATIO >1 | AVERAGE F/R INTENSITY RATIO | STANDARD DEVIATION OF F/R INTENSITY RATIO |
|---|---|---|---|---|---|---|
| A | 0 | 1 HOUR AFTER PCR | 9 | 0 | 0.50 | 0.05 |
| B | 75 | 1 HOUR AFTER PCR | 10 | 10 | 1.75 | 0.10 |

TABLE 2-continued

| GROUP | HAPLOID GENE EQUIVALENTS PER CAPILLARY | TIME WHEN FLUORESCENCE ANALYZED | NUMBER OF CAPILLARIES | NUMBER OF CAPILLARIES WITH MAXIMUM F/R INTENSITY RATIO >1 | AVERAGE F/R INTENSITY RATIO | STANDARD DEVIATION OF F/R INTENSITY RATIO |
|---|---|---|---|---|---|---|
| C | 1 | BEFORE PCR | 5 | 0 | 0.51 | 0.04 |
| D | 1 | 1 HOUR AFTER PCR | 5 | 4 | 0.83 | 0.46 |
| E | 1 | 24 HOURS AFTER PCR | 5 | 3 | 0.89 | 0.23 |
| F | 1 | 48 HOURS AFTER PCR | 5 | 1 | 0.82 | 0.23 |
| G | 1 | BEFORE PCR | 5 | 0 | 0.46 | 0.03 |
| H | 1 | 1 HOUR AFTER PCR | 5 | 5 | 1.22 | 0.43 |
| I | 1 | 24 HOURS AFTER PCR | 5 | 5 | 1.14 | 0.25 |
| J | 1 | 48 HOURS AFTER PCR | 5 | 5 | 1.11 | 0.21 |

These results support a theory that the inhomogeneities were not due to smudges blocking light transmission, thermal variations during PCR, or photobleaching. It was also determined that the 30 seconds of UV irradiation used to cure the sealing glue at the ends of the capillaries did not alter the F/R ratio. Photobleaching of fluorescein (but not the rhodamine) was detectable with repeating laser scanning at the highest power, with 10 scans reducing the fluorescein signal about 10%; however, only 1 or 2 scans at this power were performed at any one location when collecting data, and thus photobleaching does not explain the inhomogeneities. To see if convection after PCR might be broadening peaks, 0.2% by weight to about 0.8% by weight low-melt agarose was added to some PCRs but no effect of the agarose was noted. A few of the capillaries fortuitously contained air bubbles that divided the sample into two or more segments. In several of these cases, the F/R intensity ratio was ≥1 on one side of a bubble and 0.5 on the other side, consistent with blocked diffusion of degraded probe.

To confirm the results of the TaqMan assay, the fluorescent dye SYBR™ Green I was substituted for the TaqMan probe. Because the fluorescence of SYBR™ Green I increases many fold in the presence of double stranded DNA, it can be used to detect double stranded PCR product, although it does not distinguish spurious product such as "primer dimmer" from desired product. The SYBR™ Green I fluorescence assay has to be performed at elevated temperature to reduce background fluorescence from non-specific annealing of primers. To do this, segments of capillaries were placed, after PCR, in about 1 ml of mineral oil in a special 35 mm petri dish, the bottom of which was made of optically clear, conducting glass coated with a thin layer of indium tin oxide available from Bioptechs, of Butler, Pa. By applying 3-4 volts across the bottom of the dish, the temperature in the oil was raised to about 70° C. Because only a portion of the bottom of the petri dish was flat and accessible in the microscope, the capillaries had to be cut after PCR into approximately 1 cm segments in order to be imaged.

Using this device, PCR product derived from single template molecules could be detected. For example, the fluorescence intensity was 155-194 in 7 capillary segments derived from a PCR containing 30 haploid genome equivalents per cm of capillary length, compared to a fluorescence intensity of 40-57 in 7 capillary segments containing no template DNA. The variability in fluorescence at 2-3 mm intervals along these capillaries was about 20%. In contrast, in 7 capillary segments derived from PCRs containing 0.3 haploid genome equivalents per cm of capillary, the fluorescence intensity varied from 49 to 136, with 4 capillary segments having fluorescence intensity <73 at all tested positions along their lengths, 2 capillary segments having fluorescence intensity >1.00 at all positions, and one capillary having a fluorescence intensity of 68 at one end increasing to 122 at the other end thereof. These results provide additional evidence that PCR products derived from single molecules can be detected and remain localized in microcapillaries for several hours after PCR.

Example 4

A device substantially similar to that depicted in FIG. 3, having a substrate and a cover comprising microscope slide coverslips, and provided with first and second patterned layers comprising cured Norland 68 UV-curable adhesive coated respectively thereon by screen printing, was filled by capillary action with a Beta-actin polymerase chain reaction solution. The substrate and coverslip were spaced apart and held together with adhesive strips and the first and second patterned layers had complementary sample chamber portions formed therein having radii of about 1 mm. A displacing fluid comprising uncured Norland 81 UV-curable adhesive was then loaded into the flow-through channel by capillary action and displaced the polymerase chain reaction solution from the flow-through channel but not from the sample chambers. The device was then exposed to UV light to cure the displacing fluid, and the sample portions were shielded from the light with a transparency laid on top of the device and having inked spots aligned with the sample chambers. The device was then thermocycled and analyzed by fluorescence microscopy as described in connection with Example 1. Six of six sample chambers estimated to contain an average of 3 copies of genomic DNA template had F/R intensity ratios greater than 1 and four of six sample chambers estimated to contain an average of 0.3 template copies had F/R intensity ratios of greater than 1.

Discussion

The results presented above provide strong evidence that the TaqMan assay can easily detect as little as 1 template molecule when the volume of the reaction is on the order of 10 nl. For 50 μm inner diameter capillaries, the reaction volume is about 20 nl per 1 cm length of capillary. Using terminal dilutions of two preparations of genomic DNA, good correlation has been found according to the invention between the number of capillaries giving positive reactions and the number of capillaries calculated to contain 1 or more template molecules. The inference of single molecule sensitivity is further supported by the observation of peaks of elevated F/R emission along the length of capillaries estimated to contain 1 or 2 template molecules. Presumably these peaks results from localized accumulation of PCR product and corresponding degraded probe.

The localized accumulations of PCR product and degraded probe remained detectable for several hours after PCR. It is believed that the narrowness of the capillaries effectively eliminates convection so that molecular movement is dominated by diffusion. Molecules the size of completely degraded probe (e.g. rhodamine-dGTP) have diffusion constants of about $3\text{-}5\times10^{-6}$ cm$^2$/sec in water at room temperature as reported in the publication of Chang, *PHYSICAL CHEMISTRY with application to Biological Systems*, MacMillan Publishing Co., New York, page 87. The diffusion constant increases with temperature as D is proportional to $kT/\eta$, where T is measured in degrees Kelvin and $\eta$, the viscosity, decreases with temperature. The viscosity of water decreases about 3-fold as temperature increases from 25° C. (298° K.) to 92° C. (365° K.); thus, D would increase about 3.25-fold over this temperature range. The root mean square distance traveled by a molecule with diffusion constant D in time t is $(2Dt)^{1/2}$ or about 2-5 mm in 2 hours for molecules the size of completely degraded probe at temperatures between 25° C. and 92° C. The PCR product, based on its molecular weight, should have a diffusion constant of about $0.45\times10^{-6}$ cm$^2$/sec and should diffuse about 3 times less far than degraded probe in the same time. These calculations indicate that, the widths of the observed fluorescent peaks are consistent with diffusion-mediated spreading of PCR product and degraded probe.

The width of peaks might be slightly larger than predicted by diffusion, due to the tendency of PCR to saturate in regions where the concentration of PCR product is high. So long as all of the amplified molecules are replicated each cycle, the progeny from a single starting template will have the same average displacement (i.e., root mean square displacement) as a collection of independent molecules, that is, they will appear to diffuse with a root mean square displacement that is proportional to the square root of the time. However, as PCR begins to saturate, molecules near the center of the distribution where concentration is high have a lower probability of being replicated than molecules near the "edge" of the distribution where concentration is low. This unequal probability of replication tends to make the distribution broader.

The diffusion model suggests that detection of single target molecules by TaqMan assay would be difficult using conventional size capillaries. A 5 mm segment (characteristic diffusion distance for degraded probe) in a 0.8 mm inner diameter capillary contains about 2.5 μl. After spreading in 1/50th of this volume (about 50 nl), the fluorescent signal obtained from single starting molecules in 50 μm inner diameter capillaries was sometimes not above the background (see Table 2, average F/R intensity at 24 and 48 hours and number of capillaries in which maximum F/R>1). Thus, PCR would have to be significantly more efficient than achieved to detect single molecules in volumes greater than 1 μl.

While limited diffusion of product and degraded probe was important for our ability to detect single starting molecules in capillaries, diffusion of reactants present in the original reaction mixture is usually not limiting for PCR; for example, at the conventional concentration of Taq polymerase used here, the average distance between polymerase molecules is about 1 μm, and polymerase molecules (MW about 100,000 Daltons) diffuse this distance in about 0.01 second. Thus, all portions of the reaction should be sampled by a polymerase molecule many times each second.

The data also shows that single DNA molecules or segments can be detected with the "TaqMan" system when PCRs are confined to volumes of 100 nanoliters or less, preferably 60 nanoliters or less, by using capillaries with small diameters and relying on the fortuitously slow rate of diffusion. Many PCR reactions with single molecule sensitivity can be performed simultaneously in small spaces by confining PCR's to small regions in 3 dimensions as described in other embodiments of the present invention. The devices of the invention can be used to measure the number of template molecules in a sample simply by counting the number of positive reactions in replicate PCRs containing terminal dilutions of sample. Due to the closed system environment which prevents carry-over contamination, and the ability to automate fluorescence detection, devices according to the present invention and methods for using the devices have significant potential for clinical uses of PCR. An assay based on presence versus absence of PCR product in replicate reactions may be more robust with respect to small changes in amplification efficiency than quantitative competitive assays or time-to-reach-threshold level assays that require assumptions about relative or absolute amplification rates.

Although the present invention has been described in connection with preferred embodiments, it will be appreciated by those skilled in the art that additions, modifications, substitutions and deletions not specifically described may be made without departing from the spirit and scope of the invention defined in the appended claims.

The invention claimed is:

1. A method comprising:
loading a sample into a fluidic device comprising a plurality of sample chambers, said sample chambers having respective volumes ranging from about 1 picoliter to about 1 microliter;
in the fluidic device, subdividing the sample into a plurality of sample portions such that respective sample portions are positioned in the respective sample chambers, such that at least one of said plurality of sample chambers contains a sample portion having a single molecule of a target nucleic acid wherein a detectable concentration of said target nucleic acid will be attained in said at least one sample chamber after a single round of amplification; and
simultaneously subjecting the sample portions loaded into said respective sample chambers to amplification conditions using at least one amplification targeting reagent positioned in said sample chambers.

2. A method as recited in claim 1, wherein said loading comprises applying centrifugal force.

3. A method as recited in claim 1, wherein said fluidic device comprises at least one flow-through surface defining at least one flow-through channel, at least a portion of said at least one flow-through surface being hydrophobic, at least a portion of at least one of said sample chambers being hydrophilic.

4. A method as recited in claim 1, wherein said fluidic device comprises at least one flow-through surface defining at least one flow-through channel, at least a portion of said at least one flow-through surface having a first affinity to said sample portions and a second affinity to a displacing fluid, at least one of said sample chambers having a third affinity to said sample portions and a fourth affinity to said displacing fluid, said second affinity being greater than said first affinity, said third affinity being greater than said fourth affinity.

5. A method as recited in claim 1, wherein said fluidic device comprises at least one flow-through channel and said method further comprises supplying a displacing fluid into said flow-through channel, whereby said displacing fluid displaces sample from said flow-through channel.

6. A method as recited in claim 1, wherein:
said loading comprises applying centrifugal force,
wherein said fluidic device comprises at least one flow-through surface defining at least one flow-through channel,
at least a portion of said at least one flow-through surface is hydrophobic,
at least a portion of at least one of said sample chambers is hydrophilic,
wherein said method further comprises supplying a displacing fluid into said flow-through channel, whereby said displacing fluid displaces sample from said flow-through channel,
at least one of said sample chambers is in communication with said flow-through channel,
at least a portion of said at least one flow-through surface has a first affinity to said sample portions and a second affinity to said displacing fluid, said second affinity being greater than said first affinity, and
at least one of said sample chambers has a third affinity to said sample portions and a fourth affinity to said displacing fluid, said third affinity being greater than said fourth affinity.

7. A method as recited in claim 1, wherein said method further comprises after said subjecting, detecting whether there is amplified product in said sample chambers.

8. A method as recited in claim 7, wherein said detecting whether there is amplified product comprises performing a procedure which generates signals having a magnitude which is higher where said detectable concentration is present than where said detectable concentration is not present.

9. A method as recited in claim 8, wherein said procedure comprises detecting fluorescence from fluor-labeled materials.

10. A method as recited in claim 8, wherein said procedure comprises detecting at least one chemical property which changes upon hybridization.

11. A method as recited in claim 8, wherein said procedure comprises evaluating at least one property selected from among the group consisting of agglutination, turbidity, phosphorescence, light scattering, light absorbance, fluorescence energy transfer, fluorescence quenching, fluorescence dequenching, time-delayed fluorescence, chemiluminescence and calorimetric evaluation.

12. A method as recited in claim 7, wherein said sample chambers comprise microcapillary devices, and wherein peaks are generated by detecting regions within said microcapillary devices in which said detectable concentration is present.

13. A method as recited in claim 7, wherein said method further comprises after said subjecting, determining a total number of said sample chambers in which there is amplified product.

14. A method as recited in claim 1, wherein at least one of said sample chambers contains at least a first amplification targeting reagent, and at least a second of said sample chambers contains at least a second amplification targeting reagent, said first amplification targeting reagent differing from said second amplification targeting reagent.

15. A method as recited in claim 1, wherein said sample chambers have a volume ranging from about 1 picoliter to about 10 picoliters.

16. A method as recited in claim 1, wherein said sample chambers have a volume ranging from about 1 picoliter to about 100 picoliters.

17. A method as recited in claim 1, wherein said sample chambers have a volume ranging from about 1 picoliter to about nanoliter.

18. A method as recited in claim 1, wherein sample chambers have a volume of about 1 picoliter to about 10 nanoliters.

19. A method as recited in claim 1, wherein at least one of said sample chambers has at least one dimension of 2 mm or less.

20. A method as recited in claim 1, wherein at least one of said sample chambers has at least one dimension of 1 mm or less.

21. A method as recited in claim 1, wherein at least one of said sample chambers has at least one dimension of 100 microns or less.

22. A method as recited in claim 1, wherein at least one of said sample chambers has at least one dimension of 20 microns or less.

23. A method as recited in claim 1, wherein at least one of said sample chambers has at least one dimension of a few microns or less.

24. A method as recited in claim 1, wherein said sample portions have a volume ranging from about 1 picoliter to about 1 microliter.

25. A method as recited in claim 1, wherein said sample portions have a volume ranging from about 1 picoliter to about 10 nanoliters.

26. A method as recited in claim 1, wherein said sample portions have a volume of ranging from about 1 picoliter to about 1 microliter.

27. A method as recited in claim 1, wherein said sample portions confined in at least one dimension by opposing barriers separated by about 2 mm or less.

28. A method as recited in claim 1, wherein said sample portions are confined in at least one dimension by opposing barriers separated by about 1 mm or less.

29. A method as recited in claim 1, wherein said sample portions are confined in at least one dimension by opposing barriers separated by about 500 microns or less.

30. A method as recited in claim 1, wherein said sample portions are confined in at least one dimension by opposing barriers separated by about 100 microns or less.

31. A method as recited in claim 1, wherein said sample portions are confined in at least one dimension by opposing barriers separated by about 20 microns or less.

32. A method as recited in claim 1, wherein said sample portions are confined in at least one dimension by opposing barriers separated by a few microns or less.

33. A method as recited in claim 1, wherein said fluidic device comprises an assembly, said assembly comprising:
    said plurality of sample chambers, said sample chambers being confined in at least one dimension by opposing barriers separated by about 500 microns or less;
    means for sealing said plurality of sample chambers to prevent evaporation and contamination of sample portions respectively confined within said plurality of sample chambers; and
    means for restraining amplification product.

34. A method as recited in claim 33, wherein said opposing barriers are separated by 100 microns or less.

35. A method as recited in claim 1, wherein said fluidic device comprises an assembly, said assembly comprising:
    said plurality of sample chambers, said sample chambers being confined in at least one dimension by opposing barriers separated by about 500 microns or less;
    means for sealing said plurality of sample chambers to prevent evaporation and contamination of sample portions respectively confined within said plurality of sample chambers; and
    means for restraining amplification product, said means for restraining amplification product comprising a patterned layer disposed on at least one of said opposing barriers and at least partially defining each of said plurality of sample chambers.

36. A method as recited in claim 35, wherein said opposing barriers are separated by 100 microns or less.

37. A method as recited in claim 1, wherein said fluidic device comprises an assembly, said assembly comprising:
    a substrate and a cover, said substrate comprising a first surface, said cover comprising a second surface, said first surface facing and being spaced from said second surface, at least one of said first surface and said second surface comprising a first material;
    a flow-through channel, said flow-through channel being positioned between said substrate and said cover,
    at least a first of said sample chambers being bounded on at least one side thereof by said first material and being in communication with said flow-through channel, said first sample chamber having a first affinity to said sample portions and a second affinity to a displacing fluid, said flow-through channel having a third affinity to said sample portions and a fourth affinity to said displacing fluid, wherein said first, second, third and fourth affinities are such that if a first of said sample portions is loaded into a first of said sample chambers and then said a fluid displaces sample from said flow-through channel, said first sample chamber would retain said first sample portion while said displacing fluid displaces sample from said flow-through channel.

38. A method as recited in claim 1, wherein said sample chambers are confined in at least one dimension by opposing barriers separated by a dimension of about 100 microns or less.

39. A method as recited in claim 1, wherein said fluidic device further comprises:

means for facilitating loading said sample portions into said sample chambers;

means for displacing sample away from open ends of said sample chambers to isolate said sample portions within said sample chambers; and means for sealing said open ends of said sample chambers immediately after displacing sample away from said open ends.

40. A method as recited in claim 1, wherein simultaneously subjecting the sample portions to said amplification conditions comprises simultaneously subjecting the sample portions to a single round of amplification.

41. A method as recited in claim 1, wherein simultaneously subjecting the sample portions to said amplification conditions comprises simultaneously subjecting the sample portions to a homogenous amplification assay comprising a single round of amplification and detection of amplified product.

\* \* \* \* \*